(12) United States Patent
Overmyer

(10) Patent No.: US 12,137,904 B2
(45) Date of Patent: Nov. 12, 2024

(54) IMPACT MECHANISM FOR GRASP CLAMP FIRE

(71) Applicant: Cilag GmbH International, Zug (CH)

(72) Inventor: Mark D. Overmyer, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 17/840,833

(22) Filed: Jun. 15, 2022

(65) Prior Publication Data
US 2023/0404577 A1 Dec. 21, 2023

(51) Int. Cl.
*A61B 17/072* (2006.01)
*A61B 34/30* (2016.01)
*A61B 17/29* (2006.01)

(52) U.S. Cl.
CPC ........ *A61B 17/07207* (2013.01); *A61B 34/30* (2016.02); *A61B 2017/07271* (2013.01); *A61B 2017/2926* (2013.01); *A61B 2034/302* (2016.02)

(58) Field of Classification Search
CPC ................ A61B 17/072; A61B 17/068; A61B 17/07207; A61B 17/2902
See application file for complete search history.

(56) References Cited

U.S. PATENT DOCUMENTS

| | | |
|---|---|---|
| 4,114,464 A | 9/1978 | Schubert et al. |
| 4,785,180 A | 11/1988 | Dietrich et al. |
| 5,021,969 A | 6/1991 | Okamura et al. |
| 5,403,312 A | 4/1995 | Yates et al. |
| 5,688,270 A | 11/1997 | Yates et al. |
| 5,709,680 A | 1/1998 | Yates et al. |
| 5,762,458 A | 6/1998 | Wang et al. |
| 5,855,553 A | 1/1999 | Tajima et al. |
| 5,855,583 A | 1/1999 | Wang et al. |
| 5,878,193 A | 3/1999 | Wang et al. |
| 6,120,433 A | 9/2000 | Mizuno et al. |
| 6,132,368 A | 10/2000 | Cooper |

(Continued)

FOREIGN PATENT DOCUMENTS

KR 20120068597 A 6/2012

OTHER PUBLICATIONS

Kurata, et al., "Time-of-flight Near-infrared Spectroscopy for Non-destructive Measurement of Internal Quality in Grapefruit," Journal, May 2013, pp. 225-228, vol. 138, Issue 3, Journal of the American Society for Horticultural Science, Japan.

(Continued)

*Primary Examiner* — Gloria R Weeks

(57) ABSTRACT

A surgical system is disclosed including an end effector and a drive system configured to effect at least one function of the end effector. The end effector includes a first jaw, a second jaw rotatable relative to said first jaw between an open configuration and a closed configuration, and a staple cartridge comprising staples removably stored therein. The drive system includes a motor and an impact mechanism including a rotary input drivable by the motor and a rotary output drivable by the rotary input. Rotation of the rotary output is configured to effect the at least one function of the end effector. The impact mechanism is configurable between a coupled state, wherein rotation of the rotary input causes corresponding rotation of the rotary output, and a slipped state, wherein the rotary input rotates relative to the rotary output.

27 Claims, 20 Drawing Sheets

(56) References Cited

U.S. PATENT DOCUMENTS

| | | | |
|---|---|---|---|
| 6,585,144 B2 * | 7/2003 | Adams | A61B 17/072 227/19 |
| 6,587,750 B2 | 7/2003 | Gerbi et al. | |
| 6,679,406 B2 * | 1/2004 | Sakai | B25B 23/045 224/904 |
| 6,804,012 B2 | 10/2004 | Gombert | |
| 6,810,281 B2 | 10/2004 | Brock et al. | |
| 6,951,535 B2 | 10/2005 | Ghodoussi et al. | |
| 7,000,818 B2 | 2/2006 | Shelton, IV et al. | |
| 7,128,254 B2 | 10/2006 | Shelton, IV et al. | |
| 7,422,139 B2 | 9/2008 | Shelton, IV et al. | |
| 7,464,849 B2 | 12/2008 | Shelton, IV et al. | |
| 7,506,791 B2 * | 3/2009 | Omaits | A61B 17/115 227/181.1 |
| 7,516,675 B2 | 4/2009 | Kurtz et al. | |
| 7,524,320 B2 | 4/2009 | Tierney et al. | |
| 7,607,557 B2 | 10/2009 | Shelton, IV et al. | |
| 7,621,730 B2 * | 11/2009 | Del Rio | F01C 21/08 418/82 |
| 7,670,334 B2 | 3/2010 | Hueil et al. | |
| 7,673,783 B2 | 3/2010 | Morgan et al. | |
| 7,681,661 B2 * | 3/2010 | Sakai | B25F 5/029 173/217 |
| 7,747,311 B2 | 6/2010 | Quaid, III | |
| 7,753,245 B2 | 7/2010 | Boudreaux et al. | |
| 7,845,537 B2 | 12/2010 | Shelton, IV et al. | |
| 7,980,443 B2 | 7/2011 | Scheib et al. | |
| 7,996,110 B2 | 8/2011 | Lipow et al. | |
| 8,063,883 B2 | 11/2011 | Senft et al. | |
| 8,079,950 B2 | 12/2011 | Stern et al. | |
| 8,210,411 B2 | 7/2012 | Yates et al. | |
| 8,215,533 B2 * | 7/2012 | Viola | A61B 17/115 227/180.1 |
| 8,220,688 B2 | 7/2012 | Laurent et al. | |
| 8,224,484 B2 | 7/2012 | Swarup et al. | |
| 8,308,040 B2 | 11/2012 | Huang et al. | |
| 8,393,514 B2 | 3/2013 | Shelton, IV et al. | |
| 8,409,223 B2 * | 4/2013 | Sorrentino | A61B 90/08 606/143 |
| 8,523,043 B2 | 9/2013 | Ullrich et al. | |
| 8,561,870 B2 | 10/2013 | Baxter, III et al. | |
| 8,608,045 B2 | 12/2013 | Smith et al. | |
| 8,684,253 B2 | 4/2014 | Giordano et al. | |
| 8,716,973 B1 | 5/2014 | Lammertse | |
| 8,733,613 B2 | 5/2014 | Huitema et al. | |
| 8,888,789 B2 | 11/2014 | Prisco et al. | |
| 8,979,872 B2 * | 3/2015 | Harris | A61B 17/083 606/139 |
| 8,996,173 B2 | 3/2015 | Itkowitz et al. | |
| 9,050,083 B2 | 6/2015 | Yates et al. | |
| 9,055,961 B2 | 6/2015 | Manzo et al. | |
| 9,072,535 B2 | 7/2015 | Shelton, IV et al. | |
| 9,101,358 B2 | 8/2015 | Kerr et al. | |
| 9,161,817 B2 | 10/2015 | Olson et al. | |
| 9,186,046 B2 | 11/2015 | Ramamurthy et al. | |
| 9,274,047 B2 | 3/2016 | Velten et al. | |
| 9,345,481 B2 | 5/2016 | Hall et al. | |
| 9,500,473 B2 | 11/2016 | Ramamurthy et al. | |
| 9,801,679 B2 * | 10/2017 | Trees | A61B 18/1445 |
| 9,808,246 B2 | 11/2017 | Shelton, IV et al. | |
| 9,812,035 B2 | 11/2017 | Stuart et al. | |
| 9,827,059 B2 | 11/2017 | Robinson et al. | |
| 9,855,060 B2 * | 1/2018 | Ardel | A61B 17/162 |
| 9,924,942 B2 | 3/2018 | Swayze et al. | |
| 10,052,766 B2 | 8/2018 | Shirakyan et al. | |
| 10,159,506 B2 | 12/2018 | Boudreaux et al. | |
| 10,198,086 B2 | 2/2019 | Parazynski et al. | |
| 10,398,434 B2 | 9/2019 | Shelton, IV et al. | |
| 10,398,517 B2 | 9/2019 | Eckert et al. | |
| 10,441,370 B2 | 10/2019 | Millman et al. | |
| 10,470,830 B2 | 11/2019 | Hill et al. | |
| 10,485,527 B2 | 11/2019 | Shelton, IV et al. | |
| 10,485,617 B2 | 11/2019 | Crawford et al. | |
| 10,499,996 B2 | 12/2019 | de Almeida Barreto | |
| 10,507,068 B2 | 12/2019 | Kopp et al. | |
| 10,524,785 B2 | 1/2020 | Zemlok et al. | |
| 10,548,679 B2 | 2/2020 | Carlson et al. | |
| 10,568,651 B2 | 2/2020 | Kostrzewski et al. | |
| 10,653,486 B2 | 5/2020 | Ishihara et al. | |
| 10,660,719 B2 | 5/2020 | De Mathelin et al. | |
| 10,792,034 B2 | 10/2020 | Scheib et al. | |
| 10,806,478 B2 | 10/2020 | Boudreaux et al. | |
| 10,835,332 B2 | 11/2020 | Manzo et al. | |
| 10,925,598 B2 | 2/2021 | Scheib et al. | |
| 10,932,772 B2 | 3/2021 | Shelton, IV et al. | |
| 10,993,729 B1 * | 5/2021 | Aman | A61B 17/1697 |
| 11,000,270 B2 | 5/2021 | Scheib et al. | |
| 11,013,563 B2 | 5/2021 | Shelton, IV et al. | |
| 11,045,175 B2 * | 6/2021 | Coelho, Jr. | A61B 34/30 |
| 11,076,923 B1 | 8/2021 | Adelman | |
| 11,213,361 B2 | 1/2022 | Denlinger et al. | |
| 11,259,793 B2 | 3/2022 | Scheib et al. | |
| 11,284,957 B2 | 3/2022 | Denlinger et al. | |
| 11,304,692 B2 | 4/2022 | Scheib | |
| 11,369,366 B2 | 6/2022 | Scheib et al. | |
| 11,419,604 B2 | 8/2022 | Scheib et al. | |
| 11,432,885 B2 | 9/2022 | Shelton, IV et al. | |
| 11,471,151 B2 | 10/2022 | Scheib et al. | |
| 11,471,229 B2 | 10/2022 | Denlinger et al. | |
| 11,490,981 B2 | 11/2022 | Denlinger et al. | |
| 11,559,298 B2 | 1/2023 | Scheib et al. | |
| 11,564,678 B2 | 1/2023 | Scheib et al. | |
| 11,571,205 B2 | 2/2023 | Scheib et al. | |
| 11,583,350 B2 | 2/2023 | Denlinger et al. | |
| 11,666,401 B2 | 6/2023 | Denlinger et al. | |
| 11,690,690 B2 | 7/2023 | Denlinger et al. | |
| 11,701,190 B2 | 7/2023 | Denlinger et al. | |
| 11,754,712 B2 | 9/2023 | Scheib | |
| 11,813,746 B2 | 11/2023 | Overmyer et al. | |
| 11,864,728 B2 | 1/2024 | Shelton, IV et al. | |
| 2003/0109857 A1 | 6/2003 | Sanchez et al. | |
| 2004/0128026 A1 | 7/2004 | Harris et al. | |
| 2004/0221674 A1 | 11/2004 | Kornelson | |
| 2004/0243147 A1 | 12/2004 | Lipow | |
| 2007/0021738 A1 | 1/2007 | Hasser et al. | |
| 2007/0144298 A1 | 6/2007 | Miller | |
| 2007/0175955 A1 | 8/2007 | Shelton et al. | |
| 2008/0001919 A1 | 1/2008 | Pascucci | |
| 2009/0090763 A1 | 4/2009 | Zemlok et al. | |
| 2010/0262162 A1 | 10/2010 | Omori | |
| 2010/0286480 A1 | 11/2010 | Peine et al. | |
| 2010/0302017 A1 | 12/2010 | Guglielmo | |
| 2011/0295242 A1 | 12/2011 | Spivey et al. | |
| 2012/0143353 A1 | 6/2012 | Kishi | |
| 2012/0154564 A1 | 6/2012 | Hoffman et al. | |
| 2012/0158011 A1 | 6/2012 | Sandhu et al. | |
| 2012/0221145 A1 | 8/2012 | Ogawa | |
| 2012/0292369 A1 * | 11/2012 | Munro, III | A61K 51/1282 227/176.1 |
| 2013/0087355 A1 * | 4/2013 | Oomori | B25B 21/02 173/94 |
| 2013/0238048 A1 | 9/2013 | Almendinger et al. | |
| 2013/0264085 A1 * | 10/2013 | Ciotti | B25F 5/005 173/29 |
| 2014/0102741 A1 * | 4/2014 | Sekino | B25B 21/02 173/181 |
| 2014/0157522 A1 * | 6/2014 | Lorini | B26B 15/00 30/228 |
| 2014/0160015 A1 | 6/2014 | Ogawa et al. | |
| 2014/0263552 A1 | 9/2014 | Hall et al. | |
| 2014/0343566 A1 | 11/2014 | Wenderow et al. | |
| 2015/0245874 A1 | 9/2015 | Hatta | |
| 2015/0366624 A1 | 12/2015 | Kostrzewski et al. | |
| 2016/0000449 A1 * | 1/2016 | Aman | A61B 17/1622 173/217 |
| 2016/0353969 A1 | 12/2016 | Kikuchi | |
| 2017/0021738 A1 | 1/2017 | Brochhaus | |
| 2017/0055819 A1 | 3/2017 | Hansen et al. | |
| 2017/0224428 A1 | 8/2017 | Kopp | |
| 2017/0239005 A1 | 8/2017 | Cohen et al. | |
| 2017/0251900 A1 | 9/2017 | Hansen et al. | |
| 2018/0049812 A1 | 2/2018 | Yates et al. | |
| 2018/0146960 A1 | 5/2018 | Shelton, IV et al. | |

(56) References Cited

U.S. PATENT DOCUMENTS

| | | |
|---|---|---|
| 2018/0147019 A1 | 5/2018 | Farritor et al. |
| 2019/0041891 A1 | 2/2019 | Parazynski |
| 2019/0201142 A1 | 7/2019 | Shelton, IV et al. |
| 2019/0307524 A1 | 10/2019 | Popovic |
| 2020/0015899 A1 | 1/2020 | Scheib et al. |
| 2020/0015900 A1 | 1/2020 | Scheib et al. |
| 2020/0015904 A1 | 1/2020 | Scheib et al. |
| 2020/0015907 A1 | 1/2020 | Scheib |
| 2020/0015917 A1 | 1/2020 | Cavalier et al. |
| 2020/0015924 A1 | 1/2020 | Scheib et al. |
| 2020/0138534 A1 | 5/2020 | Garcia Kilroy et al. |
| 2020/0289205 A1 | 9/2020 | Scheib et al. |
| 2020/0289216 A1 | 9/2020 | Denlinger et al. |
| 2020/0289228 A1 | 9/2020 | Denlinger et al. |
| 2021/0059777 A1 | 3/2021 | Overmyer et al. |
| 2022/0202437 A1 | 6/2022 | Overmyer et al. |
| 2022/0202514 A1 | 6/2022 | Boudreaux |
| 2022/0202517 A1 | 6/2022 | Overmyer et al. |
| 2023/0120099 A1* | 4/2023 | Lefavour, Jr. ......... B25B 27/146 173/216 |

OTHER PUBLICATIONS

"ATM-MPLS Networking Version 2.0, af-aic-0178.001" ATM Standard, The ATM Forum Technical Committee, published Aug. 2003.
IEEE Std 802.3-2012 (Revision of IEEE Std 802.3-2008, published Dec. 28, 2012.

* cited by examiner

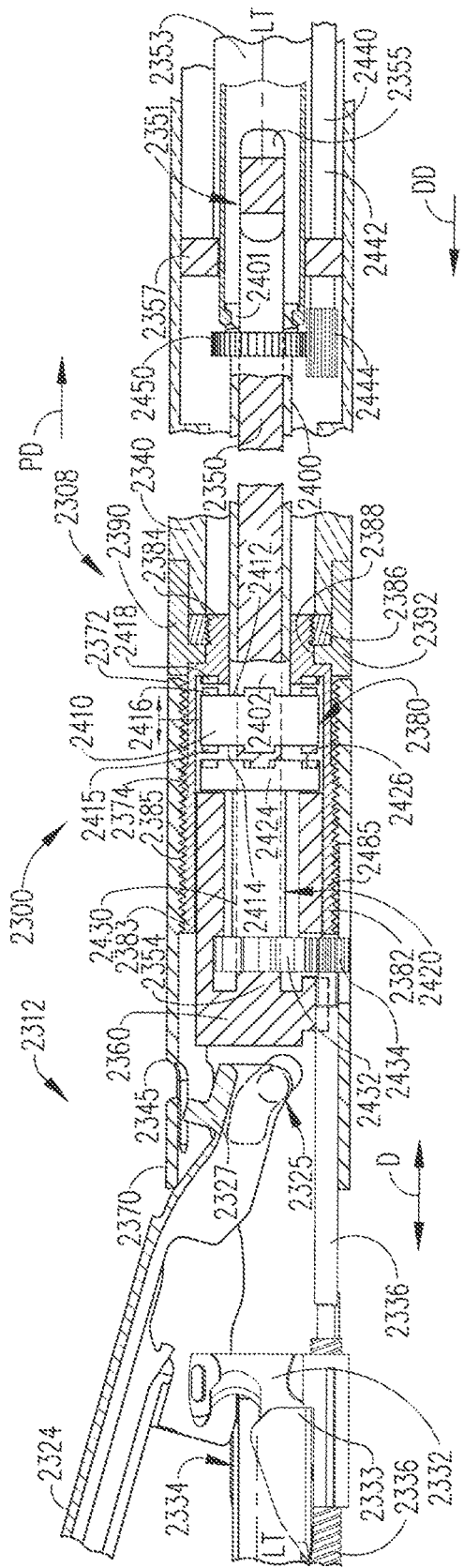
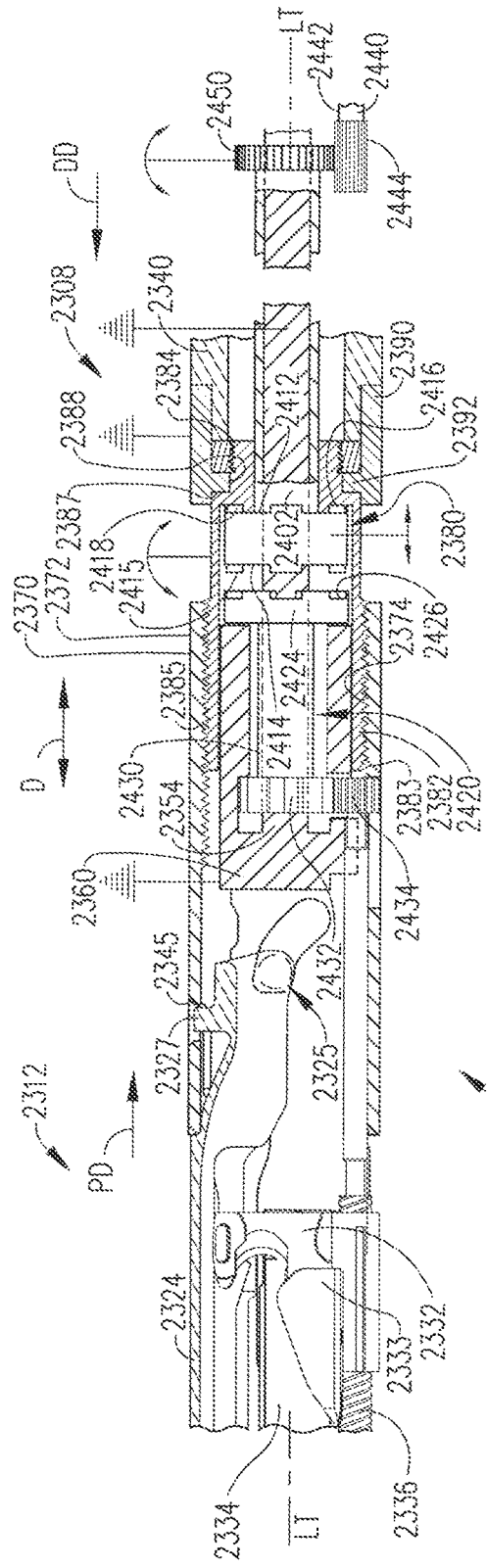
FIG. 6
FIG. 7

IMPACT MECHANISM FOR GRASP CLAMP FIRE

BACKGROUND

The present invention relates to surgical instruments and, in various arrangements, to surgical stapling and cutting instruments and staple cartridges for use therewith that are designed to staple and cut tissue.

BRIEF DESCRIPTION OF THE DRAWINGS

Various features of the embodiments described herein, together with advantages thereof, may be understood in accordance with the following description taken in conjunction with the accompanying drawings as follows:

FIG. 6 is a cross-sectional side view of a portion of the surgical end effector and elongated shaft assembly of the surgical tool embodiment of FIG. 5 with the anvil in the open position and the closure clutch assembly in a neutral position;

FIG. 7 is another cross-sectional side view of the surgical end effector and elongated shaft assembly shown in FIG. 6 with the clutch assembly engaged in a closure position;

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Figure 1:
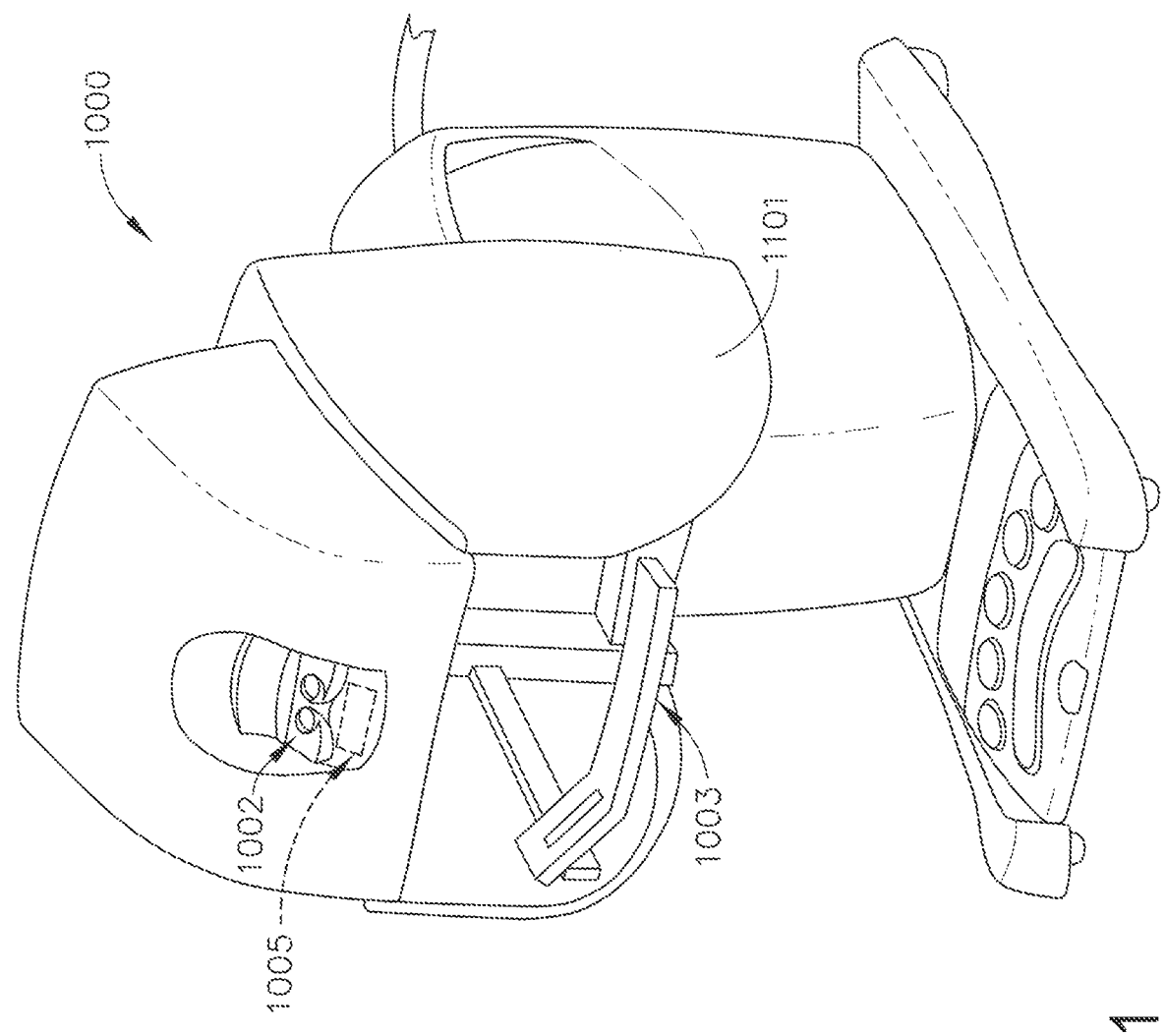
FIG. 1 is a perspective view of a robotic controller embodiment.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

A surgical stapling system can comprise a shaft and an end effector extending from the shaft. The end effector comprises a first jaw and a second jaw. The first jaw comprises a staple cartridge. The staple cartridge is insertable into and removable from the first jaw; however, other embodiments are envisioned in which a staple cartridge is not removable from, or at least readily replaceable from, the first jaw. The second jaw comprises an anvil configured to deform staples ejected from the staple cartridge. The second jaw is pivotable relative to the first jaw about a closure axis; however, other embodiments are envisioned in which the first jaw is pivotable relative to the second jaw. The surgical stapling system further comprises an articulation joint configured to permit the end effector to be rotated, or articulated, relative to the shaft. The end effector is rotatable about an articulation axis extending through the articulation joint. Other embodiments are envisioned which do not include an articulation joint.

The staple cartridge comprises a cartridge body. The cartridge body includes a proximal end, a distal end, and a deck extending between the proximal end and the distal end. In use, the staple cartridge is positioned on a first side of the tissue to be stapled and the anvil is positioned on a second side of the tissue. The anvil is moved toward the staple cartridge to compress and clamp the tissue against the deck. Thereafter, staples removably stored in the cartridge body can be deployed into the tissue. The cartridge body includes staple cavities defined therein wherein staples are removably stored in the staple cavities. The staple cavities are arranged in six longitudinal rows. Three rows of staple cavities are positioned on a first side of a longitudinal slot and three rows of staple cavities are positioned on a second side of the longitudinal slot. Other arrangements of staple cavities and staples may be possible.

The staples are supported by staple drivers in the cartridge body. The drivers are movable between a first, or unfired position, and a second, or fired, position to eject the staples from the staple cavities. The drivers are retained in the cartridge body by a retainer which extends around the bottom of the cartridge body and includes resilient members configured to grip the cartridge body and hold the retainer to the cartridge body. The drivers are movable between their unfired positions and their fired positions by a sled. The sled is movable between a proximal position adjacent the proximal end and a distal position adjacent the distal end. The sled comprises a plurality of ramped surfaces configured to slide under the drivers and lift the drivers, and the staples supported thereon, toward the anvil. In various other embodiments, the staples are formed with integral-staple drives such that the sled directly cams the staples toward the fired position. The staples with integral staple drivers can be formed by stamping the staples from a sheet of material.

Further to the above, the sled is moved distally by a firing member. The firing member is configured to contact the sled and push the sled toward the distal end. The longitudinal slot defined in the cartridge body is configured to receive the firing member. The anvil also includes a slot configured to receive the firing member. The firing member further comprises a first cam which engages the first jaw and a second cam which engages the second jaw. As the firing member is advanced distally, the first cam and the second cam can control the distance, or tissue gap, between the deck of the staple cartridge and the anvil. The firing member also comprises a knife configured to incise the tissue captured intermediate the staple cartridge and the anvil. It is desirable for the knife to be positioned at least partially proximal to the ramped surfaces such that the staples are ejected ahead of the knife.

Figure 2:
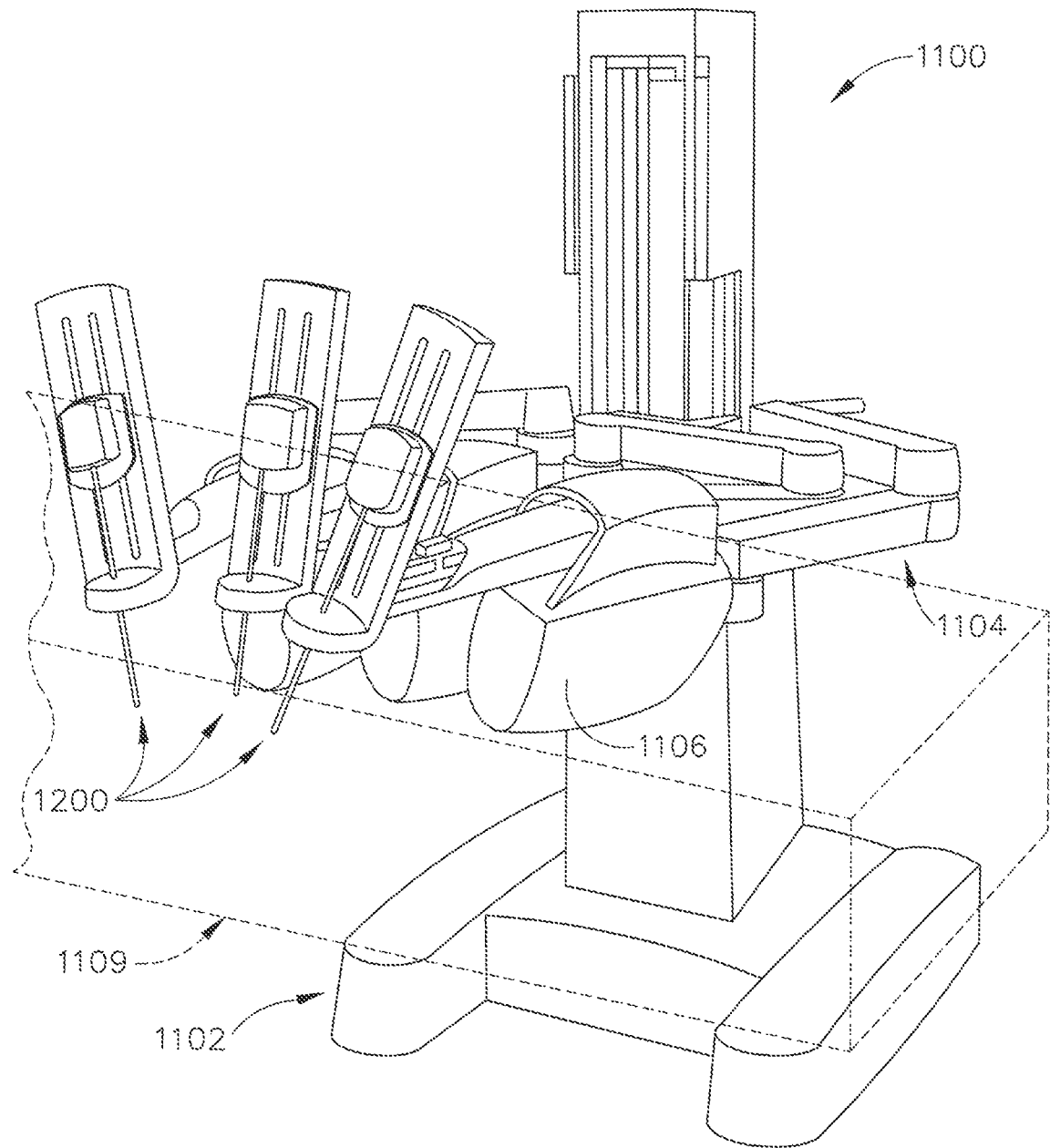
FIG. 2 is a perspective view of one robotic surgical arm cart/manipulator of a robotic system operably supporting a plurality of surgical tool embodiments of the present invention.

FIG. 1 depicts of a master controller 1001 that may be used in connection with a robotic arm slave cart 1100 of the type depicted in FIG. 2. Master controller 1001 and robotic arm slave cart 1100, as well as their respective components and control systems are collectively referred to herein as a robotic system 1000. Examples of such systems and devices are disclosed in U.S. Pat. No. 7,524,320 which has been herein incorporated by reference. Thus, various details of such devices will not be described in detail herein beyond that which may be necessary to understand various embodiments and forms of the present invention. As is known, the master controller 1001 generally includes master controllers (generally represented as 1003 in FIG. 1) which are grasped by the surgeon and manipulated in space while the surgeon views the procedure via a stereo display 1002. The master controllers 1001 generally comprise manual input devices which preferably move with multiple degrees of freedom, and which often further have an actuatable handle for actuating tools (for example, for closing grasping saws, applying an electrical potential to an electrode, or the like). Additional detail regarding the master controller 1001 and the robotic arm slave cart 1100 can be found in U.S. Pat. No. 8,684,253, which is hereby incorporated by reference in its entirety herein.

As can be seen in FIG. 2, in one form, the robotic arm cart 1100 is configured to actuate a plurality of surgical tools, generally designated as 1200. Various robotic surgery systems and methods employing master controller and robotic arm cart arrangements are disclosed in U.S. Pat. No. 6,132,368, which issued Oct. 17, 2000, entitled MULTI-COMPONENT TELEPRESENCE SYSTEM AND METHOD, the full disclosure of which is incorporated herein by reference. In various forms, the robotic arm cart 1100 includes a base 1002 from which, in the illustrated embodiment, three surgical tools 1200 are supported. In various forms, the surgical tools 1200 are each supported by a series of manually articulatable linkages, generally referred to as set-up joints 1104, and a robotic manipulator 1106. These structures are herein illustrated with protective covers extending over much of the robotic linkage. These protective covers may be optional, and may be limited in size or entirely eliminated in some embodiments to minimize the inertia that is encountered by the servo mechanisms used to manipulate such devices, to limit the volume of moving components so as to avoid collisions, and to limit the overall weight of the cart 1100. Cart 1100 will generally have dimensions suitable for transporting the cart 1100 between operating rooms. The cart 1100 may be configured to typically fit through standard operating room doors and onto standard hospital elevators. In various forms, the cart 1100 would preferably have a weight and include a wheel (or other transportation) system that allows the cart 1100 to be positioned adjacent an operating table by a single attendant.

Figure 3:
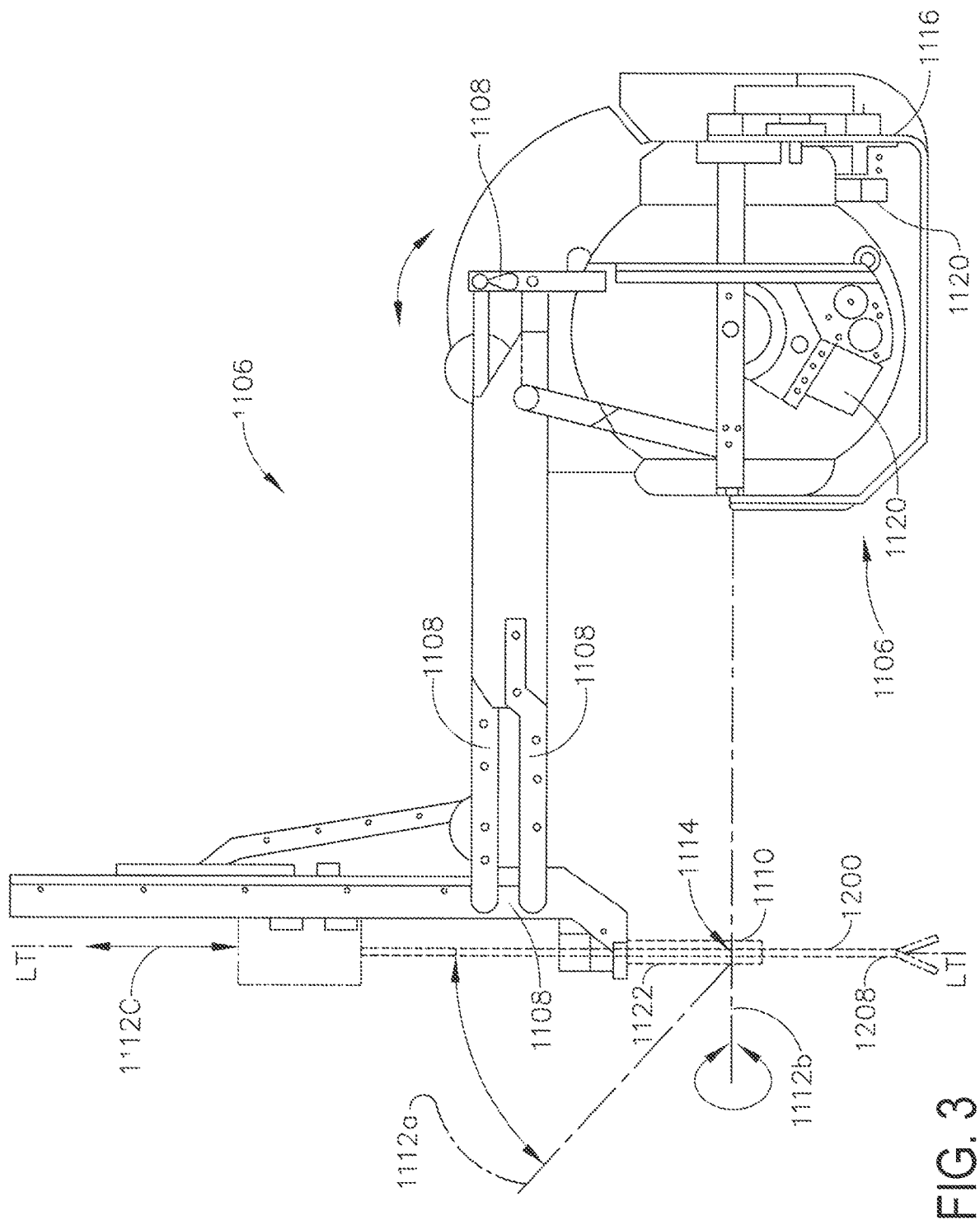
FIG. 3 is a side view of the robotic surgical arm cart/manipulator depicted in FIG. 2.

Referring now to FIG. 3, in at least one form, robotic manipulators 1106 may include a linkage 1108 that constrains movement of the surgical tool 1200. In various embodiments, linkage 1108 includes rigid links coupled together by rotational joints in a parallelogram arrangement so that the surgical tool 1200 rotates around a point in space 1110, as more fully described in issued U.S. Pat. No. 5,817,084, the full disclosure of which is herein incorporated by reference. The parallelogram arrangement constrains rotation to pivoting about an axis $1112a$, sometimes called the pitch axis. The links supporting the parallelogram linkage are pivotally mounted to set-up joints 1104 (FIG. 2) so that the surgical tool 1200 further rotates about an axis $1112b$, sometimes called the yaw axis. The pitch and yaw axes $1112a$, $1112b$ intersect at the remote center 1114, which is aligned along a shaft 1208 of the surgical tool 1200. The surgical tool 1200 may have further degrees of driven freedom as supported by manipulator 1106, including sliding motion of the surgical tool 1200 along the longitudinal tool axis "LT-LT". As the surgical tool 1200 slides along the tool axis LT-LT relative to manipulator 1106 (arrow 1112c), remote center 1114 remains fixed relative to base 1116 of manipulator 1106. Hence, the entire manipulator is generally moved to reposition remote center 1114. Linkage 1108 of manipulator 1106 is driven by a series of motors 1120. These motors actively move linkage 1108 in response to commands from a processor of a control system. As will be discussed in further detail below, motors 1120 are also employed to manipulate the surgical tool 1200.

Figure 4:
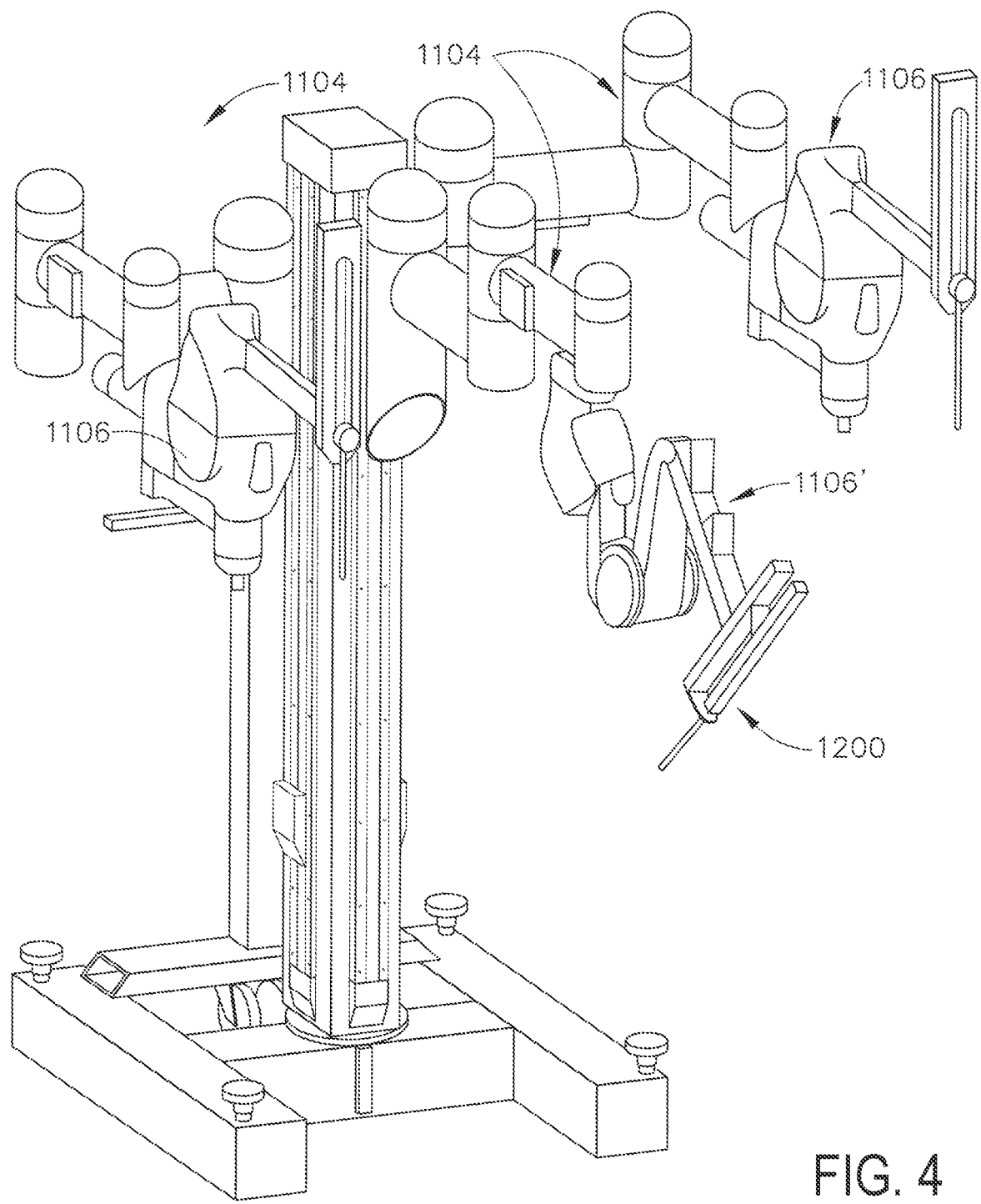
FIG. 4 is a perspective view of an exemplary cart structure with positioning linkages for operably supporting robotic manipulators that may be used with various surgical tool embodiments of the present invention.
Figure 5:
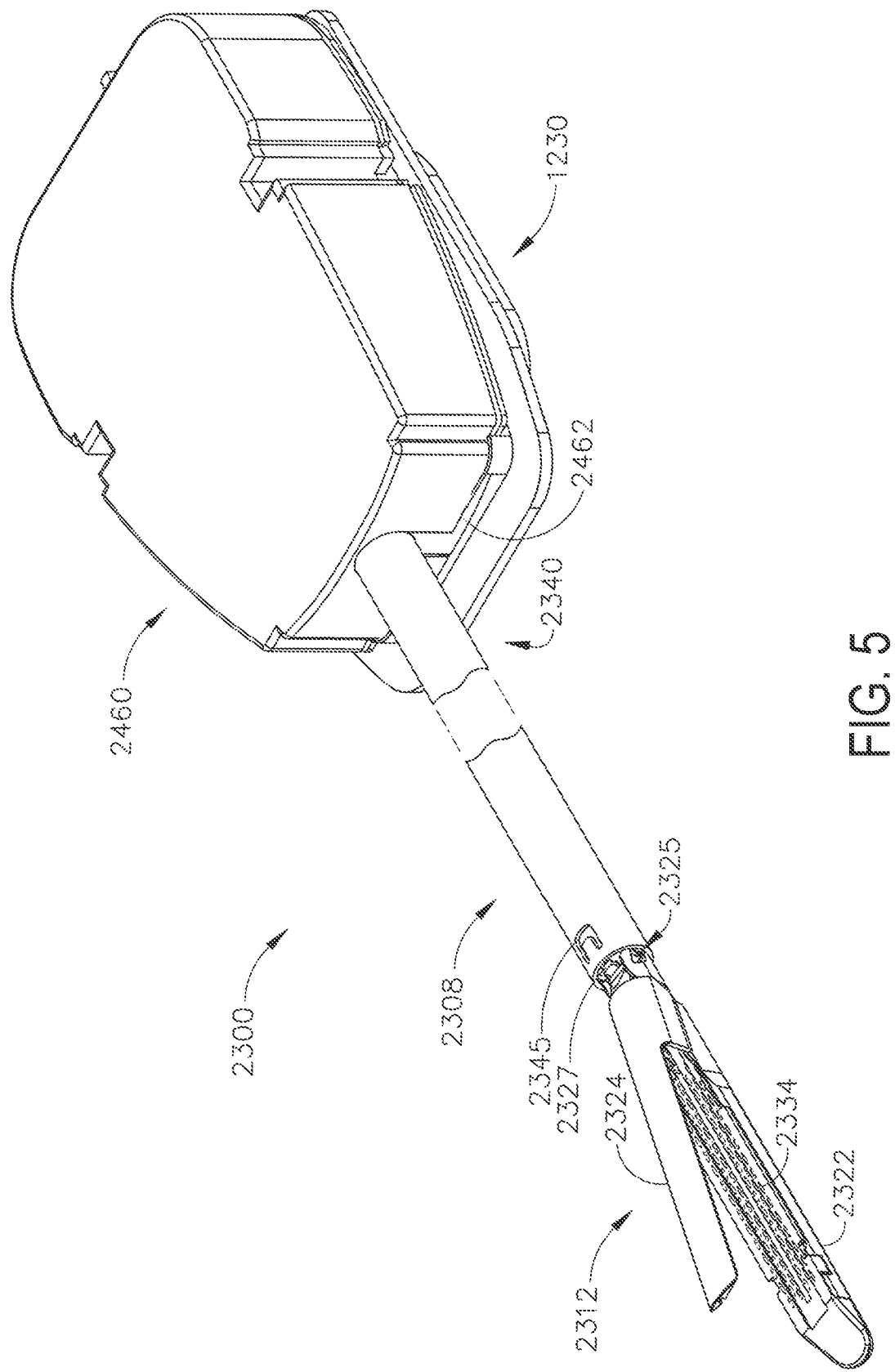
FIG. 5 is a perspective view of a surgical tool embodiment of the present invention.

An alternative set-up joint structure is illustrated in FIG. 4. In this embodiment, a surgical tool 1200 is supported by an alternative manipulator structure 1106' between two tissue manipulation tools. Those of ordinary skill in the art will appreciate that various embodiments of the present invention may incorporate a wide variety of alternative robotic structures, including those described in U.S. Pat. No. 5,878,193, which issued Mar. 2, 1999, entitled AUTOMATED ENDOSCOPE SYSTEM FOR OPTIMAL POSITIONING, the full disclosure of which is incorporated herein by reference. Additionally, while the data communication between a robotic component and the processor of the robotic surgical system is primarily described herein with reference to communication between the surgical tool 1200 and the master controller 1001, it should be understood that similar communication may take place between circuitry of a manipulator, a set-up joint, an endoscope or other image capture device, or the like, and the processor of the robotic surgical system for component compatibility verification, component-type identification, component calibration (such as off-set or the like) communication, confirmation of coupling of the component to the robotic surgical system, or the like.

FIGS. 5-9 illustrate a surgical tool 2300 that may be effectively employed in connection with the robotic system 1000 that has a tool drive assembly that is operably coupled to a controller of the robotic system that is operable by inputs from an operator and which is configured to provide at least one rotary output motion to at least one rotatable body portion supported on the tool drive assembly. In various forms, the surgical tool 2300 includes a surgical end effector 2312 that includes an elongated channel 2322 and a pivotally translatable clamping member, such as an anvil 2324, which are maintained at a spacing that assures effective stapling and severing of tissue clamped in the surgical end effector 2312. As shown in the illustrated embodiment, the surgical end effector 2312 may include, in addition to the previously-mentioned elongated channel 2322 and anvil 2324, a cutting instrument 2332 that has a sled portion 2333 formed thereon, a surgical staple cartridge 2334 that is seated in the elongated channel 2322, and a rotary end effector drive shaft 2336 that has a helical screw thread formed thereon. The cutting instrument 2332 may be, for example, a knife. As will be discussed in further detail below, rotation of the end effector drive shaft 2336 will cause the cutting instrument 2332 and sled portion 2333 to axially travel through the surgical staple cartridge 2334 to move between a starting position and an ending position. The direction of axial travel of the cutting instrument 2332 depends upon the direction in which the end effector drive shaft 2336 is rotated. The anvil 2324 may be pivotably opened and closed at a pivot point 2325 connected to the proximate end of the elongated channel 2322. The anvil 2324 may also include a tab 2327 at its proximate end that operably interfaces with a component of the mechanical closure system (described further below) to open and close the anvil 2324. When the end effector drive shaft 2336 is rotated, the cutting instrument 2332 and sled 2333 will travel longitudinally through the surgical staple cartridge 2334 from the starting position to the ending position, thereby cutting tissue clamped within the surgical end effector 2312. The movement of the sled 2333 through the surgical staple cartridge 2334 causes the staples therein to be driven through the severed tissue and against the closed anvil 2324, which turns the staples to fasten the severed tissue. In one form, the elongated channel 2322 and the anvil 2324 may be made of an electrically conductive material (such as metal) so that they may serve as part of the antenna that communicates with sensor(s) in the end effector, as described above. The surgical staple cartridge 2334 could be made of a nonconductive material (such as plastic) and the sensor may be connected to or disposed in the surgical staple cartridge 2334, as described above.

It should be noted that although the embodiments of the surgical tool 2300 described herein employ a surgical end effector 2312 that staples the severed tissue, in other embodiments different techniques for fastening or sealing the severed tissue may be used. For example, end effectors that use RF energy or adhesives to fasten the severed tissue may also be used. U.S. Pat. No. 5,709,680, which issued Jan. 20, 1998, entitled ELECTROSURGICAL HEMOSTATIC DEVICE, and U.S. Pat. No. 5,688,270, which issued Nov. 18, 1997, entitled ELECTROSURGICAL HEMOSTATIC DEVICE WITH RECESSED AND/OR OFFSET ELECTRODES, which are incorporated herein by reference, discloses cutting instruments that use RF energy to fasten the severed tissue. U.S. patent application Ser. No. 11/267,811, filed Nov. 4, 2005, now U.S. Pat. No. 7,673,783 and U.S. patent application Ser. No. 11/267,383, filed Nov. 4, 2005, now U.S. Pat. No. 7,607,557, which are also incorporated herein by reference, disclose cutting instruments that use adhesives to fasten the severed tissue. Accordingly, although the description herein refers to cutting/stapling operations and the like, it should be recognized that this is an exemplary embodiment and is not meant to be limiting. Other tissue-fastening techniques may also be used.

In the illustrated embodiment, the surgical end effector 2312 is coupled to an elongated shaft assembly 2308 that is coupled to a tool mounting portion 2460 and defines a longitudinal tool axis LT-LT. In this embodiment, the elongated shaft assembly 2308 does not include an articulation joint. Those of ordinary skill in the art will understand that other embodiments may have an articulation joint therein. In at least one embodiment, the elongated shaft assembly 2308 comprises a hollow outer tube 2340 that is rotatably supported on a tool mounting plate 2462 of a tool mounting portion 2460 as will be discussed in further detail below. In various embodiments, the elongated shaft assembly 2308 further includes a distal spine shaft 2350. Distal spine shaft 2350 has a distal end portion 2354 that is coupled to, or otherwise integrally formed with, a distal stationary base portion 2360 that is non-movably coupled to the channel 2322. See FIGS. 6-8.

As shown in FIG. 6, the distal spine shaft 2350 has a proximal end portion 2351 that is slidably received within a slot 2355 in a proximal spine shaft 2353 that is non-movably supported within the hollow outer tube 2340 by at least one support collar 2357. As can be further seen in FIGS. 6 and 7, the surgical tool 2300 includes a closure tube 2370 that is constrained to only move axially relative to the distal stationary base portion 2360. The closure tube 2370 has a proximal end 2372 that has an internal thread 2374 formed therein that is in threaded engagement with a transmission arrangement, generally depicted as 2375 that is operably supported on the tool mounting plate 2462. In various forms, the transmission arrangement 2375 includes a rotary drive shaft assembly, generally designated as 2381. When rotated, the rotary drive shaft assembly 2381 will cause the closure tube 2370 to move axially as will be describe in further detail below. In at least one form, the rotary drive shaft assembly 2381 includes a closure drive nut 2382 of a closure clutch assembly generally designated as 2380. More specifically, the closure drive nut 2382 has a proximal end portion 2384 that is rotatably supported relative to the outer tube 2340 and is in threaded engagement with the closure tube 2370. For assembly purposes, the proximal end portion 2384 may be threadably attached to a retention ring 2386. Retention ring 2386, in cooperation with an end 2387 of the closure drive nut 2382, defines an annular slot 2388 into which a shoulder 2392 of a locking collar 2390 extends. The locking collar 2390 is non-movably attached (e.g., welded, glued, etc.) to the end of the outer tube 2340. Such arrangement serves to affix the closure drive nut 2382 to the outer tube 2340 while enabling the closure drive nut 2382 to rotate relative to the outer tube 2340. The closure drive nut 2382 further has a distal end 2383 that has a threaded portion 2385 that threadably engages the internal thread 2374 of the closure tube 2370. Thus, rotation of the closure drive nut 2382 will cause the closure tube 2370 to move axially as represented by arrow "D" in FIG. 7.

Closure of the anvil 2324 and actuation of the cutting instrument 2332 are accomplished by control motions that are transmitted by a hollow drive sleeve 2400. As can be seen in FIGS. 6 and 7, the hollow drive sleeve 2400 is rotatably and slidably received on the distal spine shaft 2350. The drive sleeve 2400 has a proximal end portion 2401 that is rotatably mounted to the proximal spine shaft 2353 that protrudes from the tool mounting portion 2460 such that the drive sleeve 2400 may rotate relative thereto. See FIG. 6. As can also be seen in FIGS. 6-8, the drive sleeve 2400 is rotated about the longitudinal tool axis "LT-LT" by a drive shaft 2440. The drive shaft 2440 has a drive gear 2444 that is attached to its distal end 2442 and is in meshing engagement with a driven gear 2450 that is attached to the drive sleeve 2400.

The drive sleeve 2400 further has a distal end portion 2402 that is coupled to a closure clutch 2410 portion of the closure clutch assembly 2380 that has a proximal face 2412 and a distal face 2414. The proximal face 2412 has a series of proximal teeth 2416 formed thereon that are adapted for selective engagement with corresponding proximal teeth cavities 2418 formed in the proximal end portion 2384 of the closure drive nut 2382. Thus, when the proximal teeth 2416 are in meshing engagement with the proximal teeth cavities 2418 in the closure drive nut 2382, rotation of the drive sleeve 2400 will result in rotation of the closure drive nut 2382 and ultimately cause the closure tube 2370 to move axially as will be discussed in further detail below.

Figure 8:
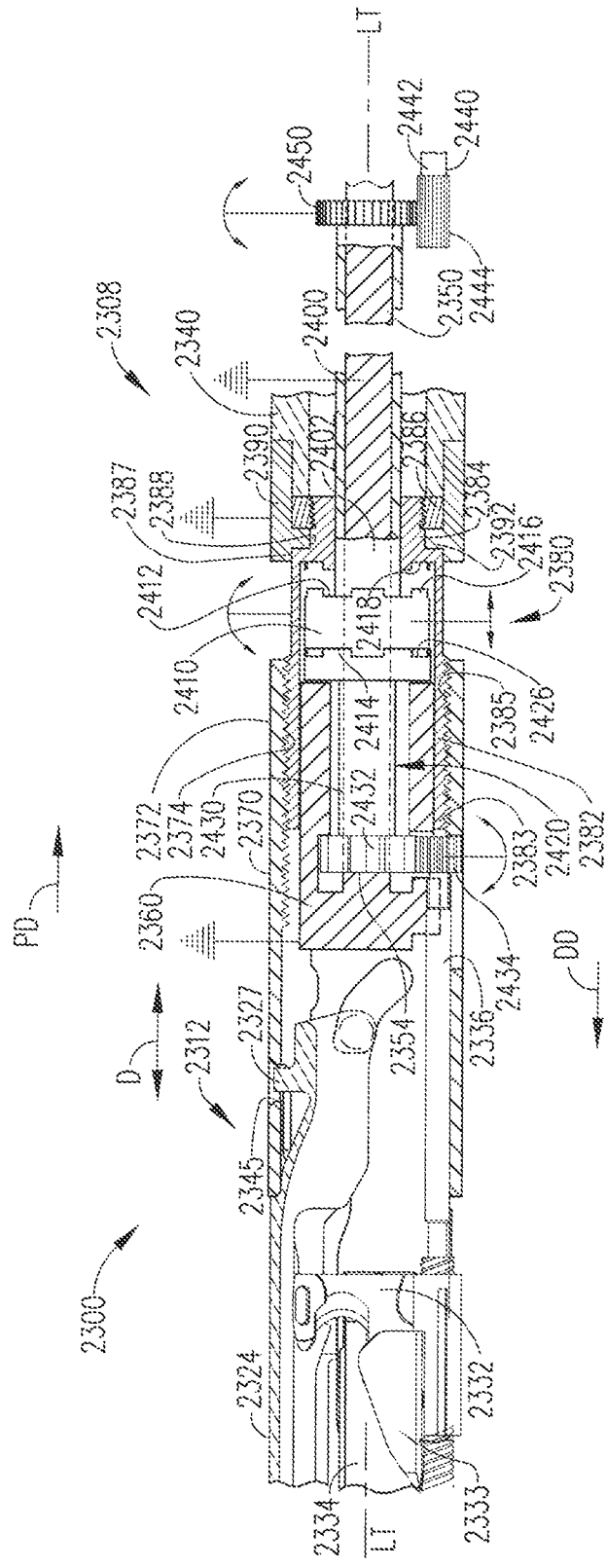
FIG. 8 is another cross-sectional side view of the surgical end effector and elongated shaft assembly shown in FIG. 6 with the clutch assembly engaged in a firing position.

As can be most particularly seen in FIGS. 6 and 7, the distal face 2414 of the drive clutch portion 2410 has a series of distal teeth 2415 formed thereon that are adapted for selective engagement with corresponding distal teeth cavities 2426 formed in a face plate portion 2424 of a knife drive shaft assembly 2420. In various embodiments, the knife drive shaft assembly 2420 comprises a hollow knife shaft segment 2430 that is rotatably received on a corresponding portion of the distal spine shaft 2350 that is attached to or protrudes from the stationary base 2360. When the distal teeth 2415 of the closure clutch portion 2410 are in meshing engagement with the distal teeth cavities 2426 in the face plate portion 2424, rotation of the drive sleeve 2400 will result in rotation of the drive shaft segment 2430 about the stationary shaft 2350. As can be seen in FIGS. 6-8, a knife drive gear 2432 is attached to the drive shaft segment 2430 and is meshing engagement with a drive knife gear 2434 that is attached to the end effector drive shaft 2336. Thus, rotation of the drive shaft segment 2430 will result in the rotation of the end effector drive shaft 2336 to drive the cutting instrument 2332 and sled 2333 distally through the surgical staple cartridge 2334 to cut and staple tissue clamped within the surgical end effector 2312. The sled 2333 may be made of, for example, plastic, and may have a sloped distal surface. As the sled 2333 traverses the elongated channel 2322, the sloped forward surface of the sled 2333 pushes up or "drive" the staples in the surgical staple cartridge 2334 through the clamped tissue and against the anvil 2324. The anvil 2324 turns or "forms" the staples, thereby stapling the severed tissue. As used herein, the term "fire" refers to the initiation of actions required to drive the cutting instrument and sled portion in a distal direction through the surgical staple cartridge to cut the tissue clamped in the surgical end effector and drive the staples through the severed tissue.

Figure 9:
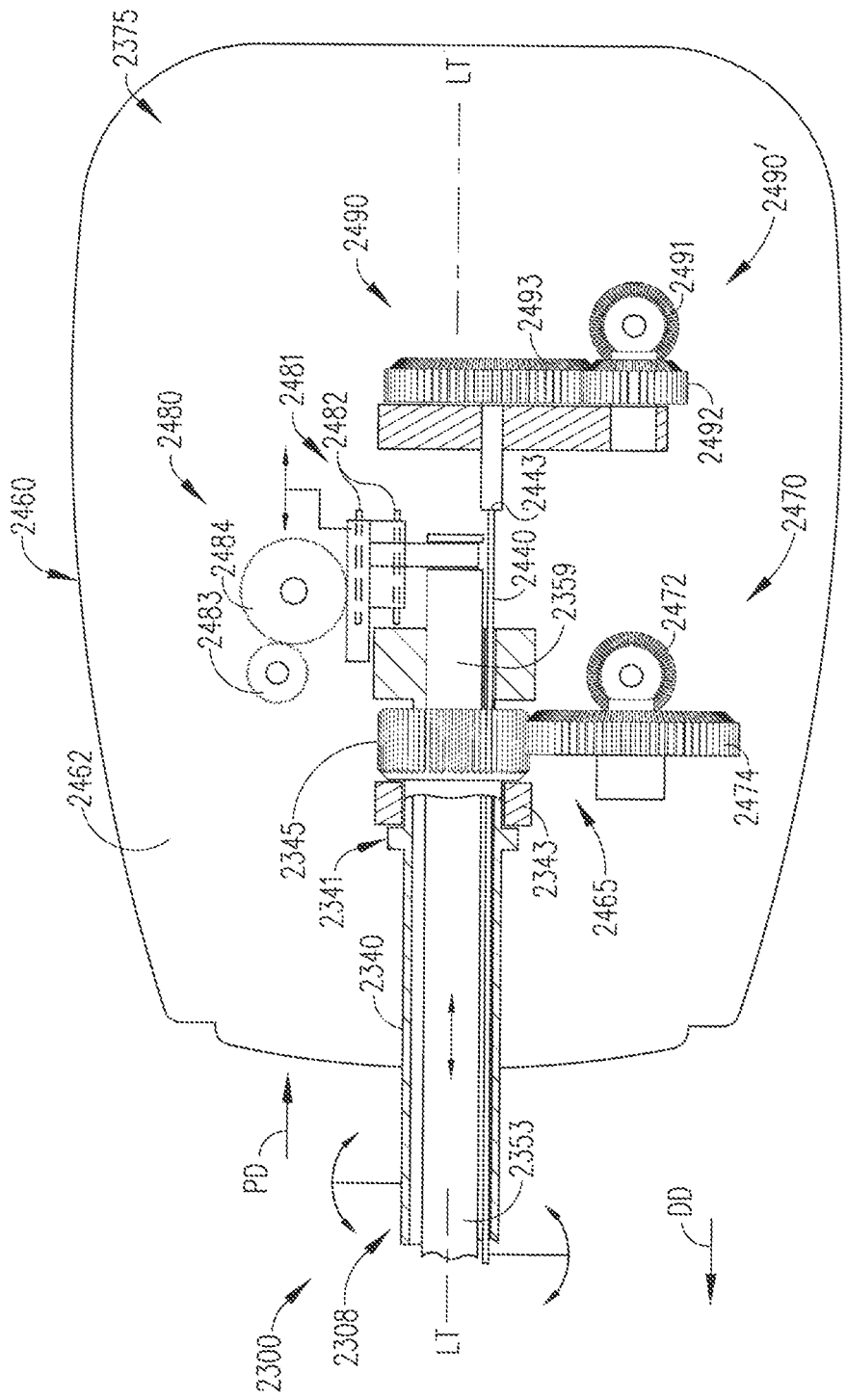
FIG. 9 is a top view of a portion of a tool mounting portion embodiment of the present invention.

In use, it may be desirable to rotate the surgical end effector 2312 about the longitudinal tool axis LT-LT. In at least one embodiment, the transmission arrangement 2375 includes a rotational transmission assembly 2465 that is configured to receive a corresponding rotary output motion from the tool drive assembly 1010 of the robotic system 1000 and convert that rotary output motion to a rotary control motion for rotating the elongated shaft assembly 2308 (and surgical end effector 2312) about the longitudinal tool axis LT-LT. As can be seen in FIG. 9, a proximal end 2341 of the outer tube 2340 is rotatably supported within a cradle arrangement 2343 attached to the tool mounting plate 2462 of the tool mounting portion 2460. A rotation gear 2345 is formed on or attached to the proximal end 2341 of the outer tube 2340 of the elongated shaft assembly 2308 for meshing engagement with a rotation gear assembly 2470 operably supported on the tool mounting plate 2462. In at least one embodiment, a rotation drive gear 2472 is coupled to a corresponding first one of the driven discs or elements on the adapter side of the tool mounting plate 2462 when the tool mounting portion 2460 is coupled to the tool drive assembly 1010. The rotation drive assembly 2470 further comprises a rotary driven gear 2474 that is rotatably supported on the tool mounting plate 2462 in meshing engagement with the rotation gear 2345 and the rotation drive gear 2472. Application of a first rotary output motion from the robotic system 1000 through the tool drive assembly 1010 to the corresponding driven element will thereby cause rotation of the rotation drive gear 2472 by virtue of being operably coupled thereto. Rotation of the rotation drive gear 2472 ultimately results in the rotation of the elongated shaft assembly 2308 (and the end effector 2312) about the longitudinal tool axis LT-LT (primary rotary motion).

Closure of the anvil 2324 relative to the staple cartridge 2034 is accomplished by axially moving the closure tube 2370 in the distal direction "DD". Axial movement of the closure tube 2370 in the distal direction "DD" is accomplished by applying a rotary control motion to the closure drive nut 2382. To apply the rotary control motion to the closure drive nut 2382, the closure clutch 2410 must first be brought into meshing engagement with the proximal end portion 2384 of the closure drive nut 2382. In various embodiments, the transmission arrangement 2375 further includes a shifter drive assembly 2480 that is operably supported on the tool mounting plate 2462. More specifically and with reference to FIG. 47, it can be seen that a proximal end portion 2359 of the proximal spine portion 2353 extends through the rotation gear 2345 and is rotatably coupled to a shifter gear rack 2481 that is slidably affixed to the tool mounting plate 2462 through slots 2482. The shifter drive assembly 2480 further comprises a shifter drive gear 2483 that is coupled to a corresponding second one of the driven discs or elements on the adapter side of the tool mounting plate 2462 when the tool mounting portion 2460 is coupled to the tool holder. The shifter drive assembly 2480 further comprises a shifter driven gear 2478 that is rotatably supported on the tool mounting plate 2462 in meshing engagement with the shifter drive gear 2483 and the shifter rack gear 2482. Application of a second rotary output motion from the robotic system 1000 through the tool drive assembly 1010 to the corresponding driven element will thereby cause rotation of the shifter drive gear 2483 by virtue of being operably coupled thereto. Rotation of the shifter drive gear 2483 ultimately results in the axial movement of the shifter gear rack 2482 and the proximal spine portion 2353 as well as the drive sleeve 2400 and the closure clutch 2410 attached thereto. The direction of axial travel of the closure clutch 2410 depends upon the direction in which the shifter drive gear 2483 is rotated by the robotic system 1000. Thus, rotation of the shifter drive gear 2483 in a first rotary direction will result in the axial movement of the closure clutch 2410 in the proximal direction "PD" to bring the proximal teeth 2416 into meshing engagement with the proximal teeth cavities 2418 in the closure drive nut 2382. Conversely, rotation of the shifter drive gear 2483 in a second rotary direction (opposite to the first rotary direction) will result in the axial movement of the closure clutch 2410 in the distal direction "DD" to bring the distal teeth 2415 into meshing engagement with corresponding distal teeth cavities 2426 formed in the face plate portion 2424 of the knife drive shaft assembly 2420.

Once the closure clutch 2410 has been brought into meshing engagement with the closure drive nut 2382, the closure drive nut 2382 is rotated by rotating the closure clutch 2410. Rotation of the closure clutch 2410 is controlled by applying rotary output motions to a rotary drive transmission portion 2490 of transmission arrangement 2375 that is operably supported on the tool mounting plate 2462 as shown in FIG. 9. In at least one embodiment, the rotary drive transmission 2490 includes a rotary drive assembly 2490' that includes a gear 2491 that is coupled to a corresponding third one of the driven discs or elements on the adapter side of the tool mounting plate 2462 when the tool mounting portion 2460 is coupled to the tool holder. The rotary drive transmission 2490 further comprises a first rotary driven gear 2492 that is rotatably supported on the tool mounting plate 2462 in meshing engagement with a second rotary driven gear 2493 and the rotary drive gear 2491. The second rotary driven gear 2493 is coupled to a proximal end portion 2443 of the drive shaft 2440.

Rotation of the rotary drive gear 2491 in a first rotary direction will result in the rotation of the drive shaft 2440 in a first direction. Conversely, rotation of the rotary drive gear 2491 in a second rotary direction (opposite to the first rotary direction) will cause the drive shaft 2440 to rotate in a second direction. As indicated above, the drive shaft 2440 has a drive gear 2444 that is attached to its distal end 2442 and is in meshing engagement with a driven gear 2450 that is attached to the drive sleeve 2400. Thus, rotation of the drive shaft 2440 results in rotation of the drive sleeve 2400.

A method of operating the surgical tool 2300 will now be described. Once the tool mounting portion 2462 has been operably coupled to the tool holder of the robotic system 1000 and oriented into position adjacent the target tissue to be cut and stapled, if the anvil 2334 is not already in the open position (FIG. 6), the robotic system 1000 may apply the first rotary output motion to the shifter drive gear 2483 which results in the axial movement of the closure clutch 2410 into meshing engagement with the closure drive nut 2382 (if it is not already in meshing engagement therewith). See FIG. 7. Once the controller 1001 of the robotic system 1000 has confirmed that the closure clutch 2410 is meshing engagement with the closure drive nut 2382 (e.g., by means of sensor(s)) in the surgical end effector 2312 that are in communication with the robotic control system), the robotic controller 1001 may then apply a second rotary output motion to the rotary drive gear 2492 which, as was described above, ultimately results in the rotation of the rotary drive nut 2382 in the first direction which results in the axial travel of the closure tube 2370 in the distal direction "DD". As the closure tube 2370 moved in the distal direction, it contacts a portion of the anvil 2323 and causes the anvil 2324 to pivot to the closed position to clamp the target tissue between the anvil 2324 and the surgical staple cartridge 2334. Once the robotic controller 1001 determines that the anvil 2334 has been pivoted to the closed position by corresponding sensor(s) in the surgical end effector 2312 in communication therewith, the robotic system 1000 discontinues the application of the second rotary output motion to the rotary drive gear 2491. The robotic controller 1001 may also provide the surgeon with an indication that the anvil 2334 has been fully closed. The surgeon may then initiate the firing procedure. In alternative embodiments, the firing procedure may be automatically initiated by the robotic controller 1001. The robotic controller 1001 then applies the primary rotary control motion 2483 to the shifter drive gear 2483 which results in the axial movement of the closure clutch 2410 into meshing engagement with the face plate portion 2424 of the knife drive shaft assembly 2420. See FIG. 8. Once the controller 1001 of the robotic system 1000 has confirmed that the closure clutch 2410 is meshing engagement with the face plate portion 2424 (by means of sensor(s)) in the end effector 2312 that are in communication with the robotic controller 1001), the robotic controller 1001 may then apply the second rotary output motion to the rotary drive gear 2492 which, as was described above, ultimately results in the axial movement of the cutting instrument 2332 and sled portion 2333 in the distal direction "DD" through the surgical staple cartridge 2334. As the cutting instrument 2332 moves distally through the surgical staple cartridge 2334, the tissue clamped therein is severed. As the sled portion 2333 is driven distally, it causes the staples within the surgical staple cartridge to be driven through the severed tissue into forming contact with the anvil 2324. Once the robotic controller 1001 has determined that the cutting instrument 2324 has reached the end position within the surgical staple cartridge 2334 (by means of sensor(s)) in the end effector 2312 that are in communication with the robotic controller 1001), the robotic controller 1001 discontinues the application of the second rotary output motion to the rotary drive gear 2491. Thereafter, the robotic controller 1001 applies the secondary rotary output motion to the rotary drive gear 2491 which ultimately results in the axial travel of the cutting instrument 2332 and sled portion 2333 in the proximal direction "PD" to the starting position. Once the robotic controller 1001 has determined that the cutting instrument 2324 has reached the starting position by means of sensor(s) in the surgical end effector 2312 that are in communication with the robotic controller 1001, the robotic controller 1001 discontinues the application of the secondary rotary output motion to the rotary drive gear 2491. Thereafter, the robotic controller 1001 applies the primary rotary output motion to the shifter drive gear 2483 to cause the closure clutch 2410 to move into engagement with the rotary drive nut 2382. Once the closure clutch 2410 has been moved into meshing engagement with the rotary drive nut 2382, the robotic controller 1001 then applies the secondary output motion to the rotary drive gear 2491 which ultimately results in the rotation of the rotary drive nut 2382 in the second direction to cause the closure tube 2370 to move in the proximal direction "PD". As can be seen in FIGS. 6-8, the closure tube 2370 has an opening 2345 therein that engages the tab 2327 on the anvil 2324 to cause the anvil 2324 to pivot to the open position. In alternative embodiments, a spring may also be employed to pivot the anvil 2324 to the open position when the closure tube 2370 has been returned to the starting position (FIG. 6).

In various embodiments, a single rotary input can be used to control multiple functions of an end effector of a surgical instrument. In one embodiment, as described above, rotation of the drive shaft 2440 can effect movement of the anvil 2334 to capture/release tissue in the end effector 2312 and axial movement of the cutting instrument 2332 and sled portion 2333 through the surgical staple cartridge 2334 to cut and staple tissue. In various other embodiments, the single rotary input can be used to quickly transition the first jaw and the second jaw of the end effector from an open configuration to a closed configuration at a first speed to weakly grasp tissue therebetween, enabling nimble motion for grasping and manipulating the tissue. The single rotary input can also be used to slowly transition the first jaw and the second jaw from an open configuration toward a closed configuration at a second speed slower than the first speed to strongly grasp tissue therebetween in preparation for the tissue to be stapled. The single rotary input can further be used to drive a firing assembly that can actuate a staple cartridge situated in the end effector to fire staples into the grasped tissue, while also deploying a knife to cut the stapled tissue. The variety of functions of the single rotary input puts conflicting requirements on the drive train design.

A solution for the above-identified problem is to use inertia to "smooth out" power consumption and "plow through" brief peak loads, such as during the strong grasping of tissue or the staple firing operation, while still enabling nimble motion for grasping with the jaws of the end effector. Impact driver mechanisms generate the desired peak loads required; however, these mechanisms introduce backlash that is unacceptable for weakly grasping tissue. Accordingly, it would be desirable to have an impact-style mechanism that generates the desired peak loads, but that avoids unacceptable grasping backlash.

Figure 10:
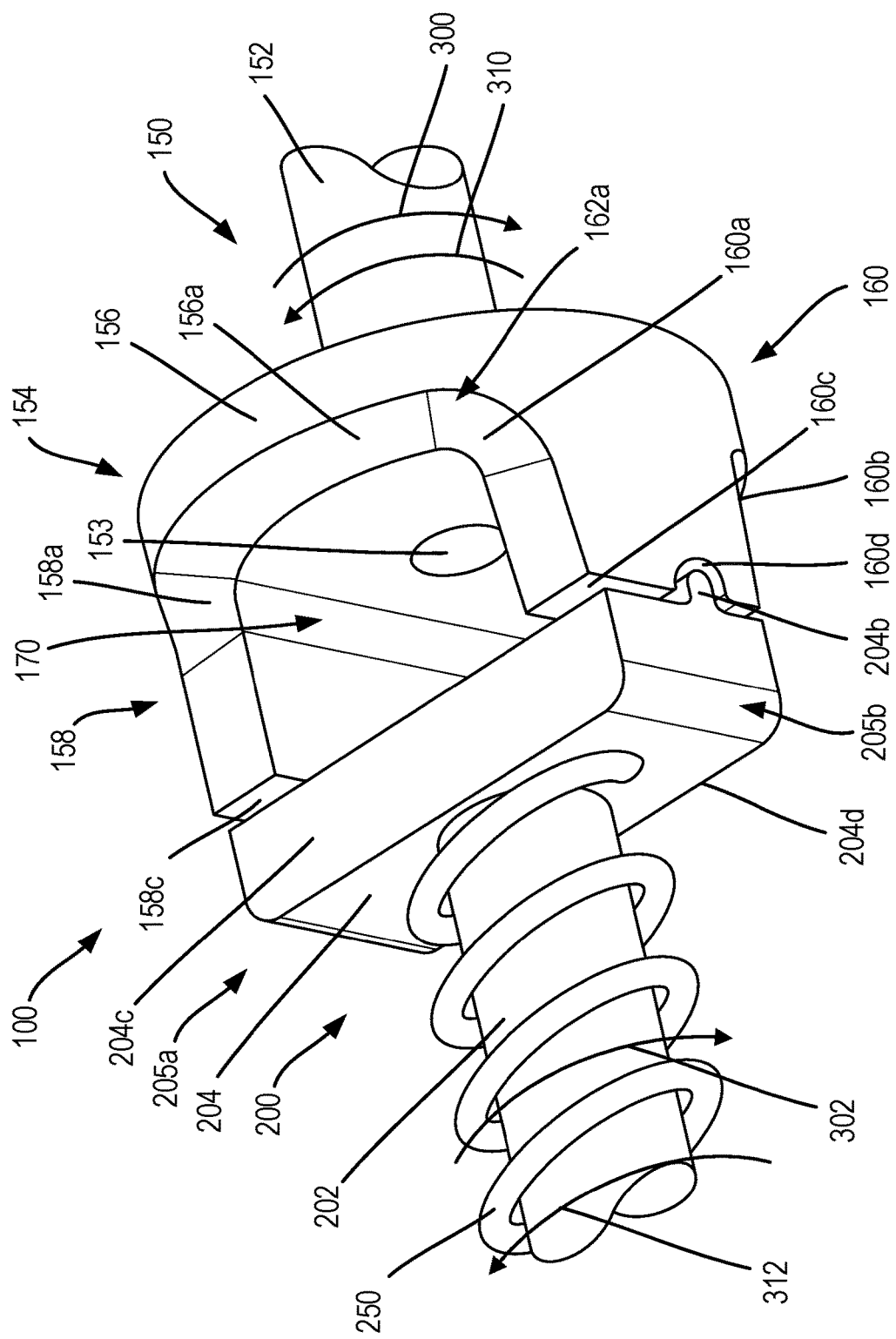
FIG. 10 is an impact mechanism in a coupled state, according to at least one aspect of the present disclosure.

In various embodiments, referring to FIG. 10, an impact mechanism 100 is provided according to at least one aspect of the present disclosure. The impact mechanism 100 includes a rotary input 150, a rotary output 200, and a compression spring 250. In various embodiments, the rotary input 150 can be rotatably driven by a motor, such as a motor in a handle assembly, such as the handle assembly in U.S. Pat. No. 7,845,537, which is hereby incorporated by reference in its entirety herein. In various embodiments, the rotary input 150 can be rotatably driven by a motor, such as a motor from a robotic surgical system, such motors in the a robotic arm cart 1100. Other embodiments are envisioned where the rotary input 150 is driven by other motion generators other than a motor, such as by a trigger of a surgical instrument, as an example.

The rotary input 150 includes a shaft 152 and an impact driver 154 extending from the shaft 152. In various embodiments, the impact driver 154 is removably coupleable to the shaft 152 at a coupling interface 153, thereby allowing the impact driver 154 to be replaced with another impact driver. The impact driver 154 includes a base 156 and two arms 158, 160 extending from the base 156. Arm 158 includes ramped cams 158a, 158b defined on each lateral side of arm 158 and a distal surface 158c extending between the ramped cams 158a, 158b. Similarly, arm 160 includes ramped cams 160a, 160b defined on each lateral side of arm 160 and a distal surface 160c extending between the ramped cams 160a, 160b. The base 156 includes a curved transition surface 156a, 156b on each lateral side thereof. The ramped cams 158a, 160a and the curved transition surface 156a define a first curved path 162a from the distal surface 158c of arm 158 to the distal surface 160c of arm 160. Similarly, the ramped cams 158b, 160b and the curved transition surface 156b define a second curved path 162b from the distal surface 158c of arm 158 to the distal surface 160c of arm 160. In addition, each arm 158, 158 includes a grasping detent 158d, 160d defined in the distal surfaces 158c, 160c sized to receive and retain a corresponding ridge of the rotary output 200, as will be explained in more detail below.

In various embodiments, the rotary output 200 includes a shaft 202 and a head 204 extending therefrom. The head 204 includes a pair of ridges 204a, 204b extending from lateral sides 205a, 205b thereof (ridge 204a cannot be seen in FIGS. 10-14, but will be referred to herein for ease of explaining the impact mechanism 100) that correspond to the grasping detents 158d, 160d defined in the distal surfaces 158c, 160c of the arms 158, 160. In various other embodiments, the head 204 includes a continuous ridge that extends from the first lateral side 205a of the head 204 to the second lateral side 205b of the head 204 as opposed to two discrete ridges that extend from discrete locations on the lateral sides 205a, 205b of the head 204. In one aspect, the head 204 defines impact faces 204c, 204d on each lateral side thereof that will be explained in more detail below.

Figure 12:
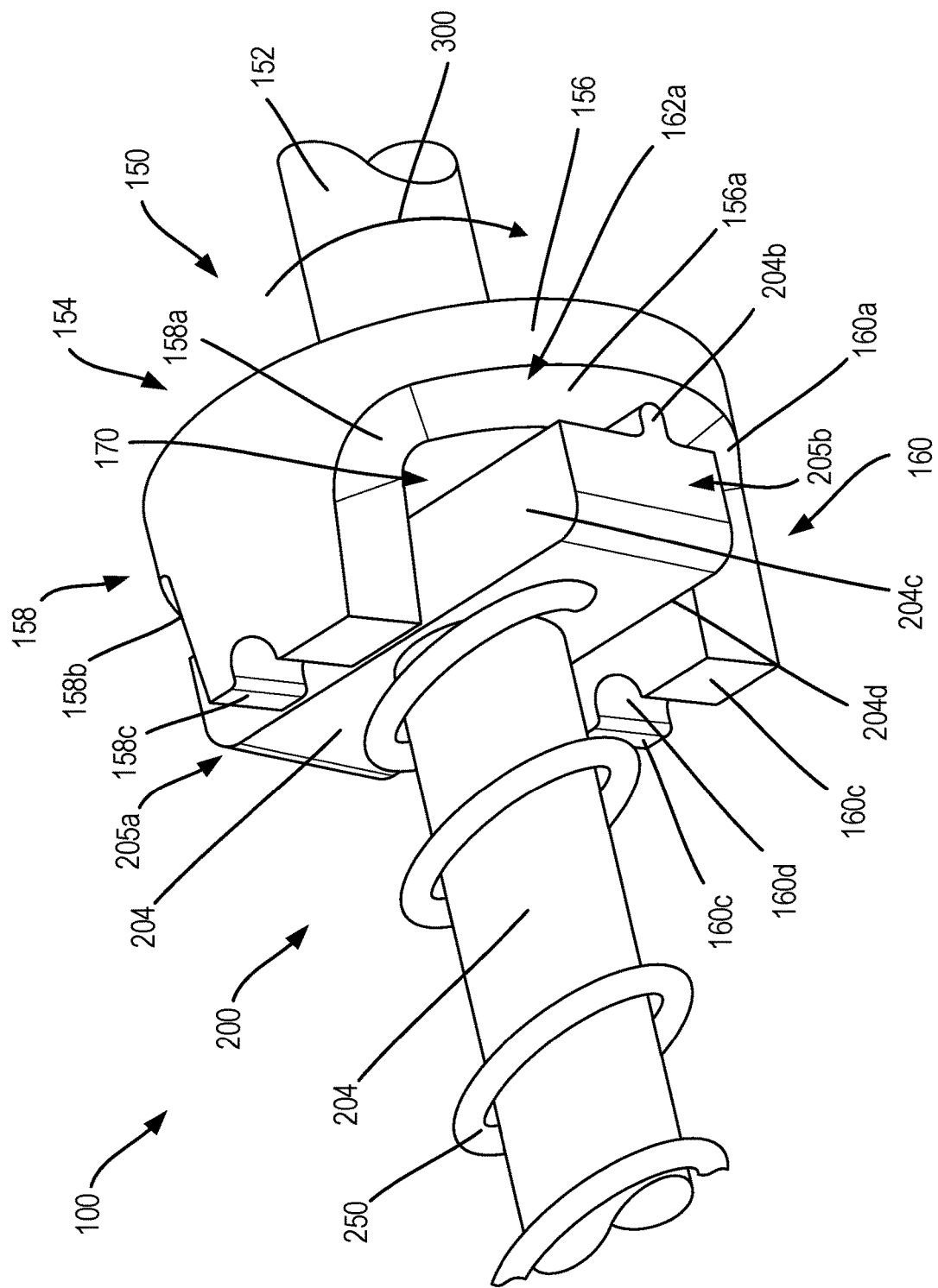
FIG. 12 is the impact mechanism of FIG. 10 with a rotary output thereof positioned within a trough of a rotary input of the impact mechanism, according to at least one aspect of the present disclosure.

As can be seen in FIG. 10, the compression spring 250 encircles the shaft 202 and applies a force to the head 204 to push the rotary output 200 toward and into operably engagement with the rotary input 150. In various embodiments, the rotary output 200 is axially movable relative to the rotary input 150 between an engaged position, as can be seen in FIG. 10, in which the compression spring 250 is compressed a first amount, and a slipped position, as can be seen in FIG. 12, in which the compression spring 250 is compressed a second amount less than the first amount.

In operation, the impact mechanism 100 can be in a coupled state, as is shown in FIG. 10, where the rotary input 150 is operably coupled to the rotary output 200 by way of the grasping detents 158d, 160d and the ridges 204a, 204b. As described above, a motor can apply input rotary motions to the rotary input 150, which can rotate the rotary input in a first direction 300, such as a clockwise direction, or a second direction 310, such as a counterclockwise direction. In the coupled state, rotation of the rotary input 150 in the first direction 300 causes the rotary input 150 to apply a torque to the rotary output 200 by way of the coupled detents 158d, 160d and ridges 204a, 204b, resulting in a corresponding directional rotation of the rotary output 200, i.e., direction 302. Similarly, in the coupled state, rotation of the rotary input 150 in the second direction 310 causes the rotary input 150 to apply a torque to the rotary output 200 by way of the coupled detents 158*d*, 160*d* and ridges 204*a*, 204*b*, resulting in a corresponding directional rotation of the rotary output 200, i.e., direction 312. In one aspect, in the coupled state, there is no relative rotation between the rotary input 150 and the rotary output 200.

Rotation of the rotary output 200 can effect a variety of end effector functions, such as moving jaws of an end effector quickly between an open configuration and a closed configuration to grasp and manipulate tissue. In one embodiment, rotation of the rotary output 200 can move the anvil 2324 and the elongated channel 2322 between and open and closed configuration, as described elsewhere herein. In one aspect, rotation of the rotary input 150 in the first direction 300 causes corresponding rotation of the rotary output 200 in the first direction 302, moving the jaws toward the open configuration. In another aspect, rotation of the rotary input in the second direction 310 causes corresponding rotation of the rotary output 200 in the second direction 312, moving the jaws toward the closed configuration.

In one aspect, rotation of the rotary output 200 can effect a variety of other end effector functions, such as slowly moving the jaws of an end effector quickly between an open configuration and a closed configuration to clamp tissue in preparation for stapling. In one aspect, rotation of the rotary input 150 in the first direction 300 causes corresponding rotation of the rotary output 200 in the first direction 302, moving the jaws toward the open configuration. In another aspect, rotation of the rotary input 150 in the second direction 310 causes corresponding rotation of the rotary output 200 in the second direction 312, moving the jaws toward the closed configuration to strongly grasp tissue.

In one aspect, rotation of the rotary output 200 can effect a variety of other end effector functions, such as actuating a firing drive to deploy staples into tissue grasped between the jaws and cut the stapled tissue. In one embodiment, rotation of the rotary output 200 can drive cutting instrument 2332 that has a sled portion 2333 formed thereon through the surgical staple cartridge 2334 to deploy staples therefrom and cut tissue within the end effector 2312, as described elsewhere herein. In one aspect, rotation of the rotary input 150 in the first direction 300 causes corresponding rotation of the rotary output 200 in the first direction 302, moving a firing drive through a staple firing stroke to deploy staples from a staple cartridge and to cut the stapled tissue. In another aspect, rotation of the rotary input 150 in the second direction 310 causes corresponding rotation of the rotary output 200 in the second direction 312, moving the firing drive toward an unfired position in preparation for a new staple cartridge to be positioned in the end effector.

Figure 11:
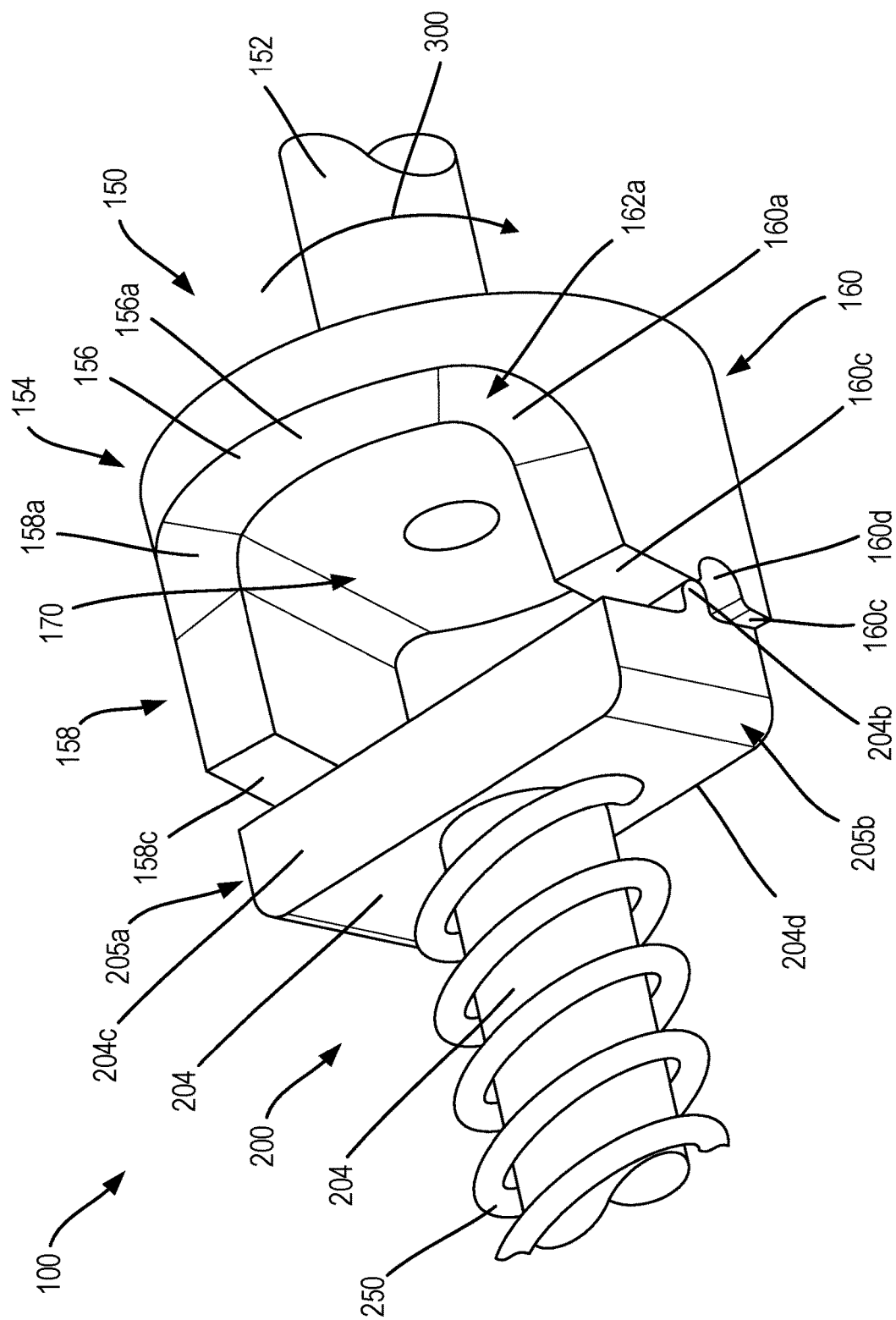
FIG. 11 is the impact mechanism of FIG. 10 in a slipped state, according to at least one aspect of the present disclosure.

In operation, when the rotary output 200 encounters resistance due to, for example, thick tissue being positioned between the jaws of the end effector, the amount of torque required to rotate the rotary output 200 increases. When the amount of torque required to rotate the rotary output 200 reaches or exceeds a torque threshold, the torque applied by the rotary input 150 can cause the compression spring 250 to slightly compress, causing the ridges 204*a*, 204*b* to "slip" out of the detents 158*d*, 160*d*, as can be seen in FIG. 11, transitioning the impact mechanism 100 to a slipped state. Once the ridges 204*a*, 204*b* have slipped from the detents, rotational motion of the rotary input 150, at least temporarily, as will be explained in more detail below, is no longer transferred to the rotary output 200. Rather, in the slipped state, the rotary input 150 rotates relative to the rotary output 200.

In one aspect, the torque threshold is based on the spring constant of the compression spring 250. In various embodiments, the impact mechanism 100 can be provided with a plurality of compression springs 250, thereby allowing a user to swap out compression springs 250 to vary the torque threshold according to the application in which the impact mechanism 100 will be utilized.

Continuing from above, rotation of the rotary input 150 in the slipped state results in relative rotation between the rotary input 150 and the rotary output 200. As a result, in the slipped state, the arms 158, 160 of the rotary input 150 rotate relative to the head 204 of the rotary output 200. Once the rotary input 150 has rotated a particular amount relative to the rotary output 200, the compression spring 250 can axially drive the head 204 of the rotary output 200 into a trough 170 defined between the arms 158, 160 of the impact driver 154, as can be seen in FIG. 12, transitioning the rotary output 200 to the slipped position, as described above. In one aspect, the particular amount of rotation can be an amount of rotation that is needed for the lateral ends 205*a*, 205*b* of the head 204 to clear the distal surfaces 158*c*, 160*c* of the arms 158, 160, allowing the head 204 to be driven into the trough 170 defined between the arms of the rotary input. In one aspect, the particular amount of rotation can be less than or equal to 15°. In one aspect, the particular amount of rotation can be between 15° and 30°, such as 20° or In one aspect, the predetermined amount of rotation can be greater than or equal to 30°, such as 45°. In one aspect, the predetermined amount of rotation can be greater than or equal to 45°, such as 50°, 75°, or 90°.

Continuing from above, with the head 204 of the rotary output 200 positioned in the trough 170 of the impact driver 154, i.e., the slipped position, the rotary input 150 can continue to rotate in the first direction 300 relative to the rotary output 200 such that the ramped camming surface 158*a* impacts the impact face 204*c* and ramped camming surface 160*b* impacts the impact face 204*d*, causing the impact driver 154 to deliver a brief peak load to the rotary output 200 that is higher than normally possible when the impact mechanism 100 is in the coupled state. In various embodiments, the brief peak load can be 1.2 times greater than what is capable when the impact mechanism 100 is in the coupled state. In various embodiments, the brief peak load can be 1.5 times greater than what is capable when the impact mechanism 100 is in the coupled state. In various embodiments, the brief peak load can be 2 times greater than what is capable when the impact mechanism 100 is in the coupled state.

Figure 13:
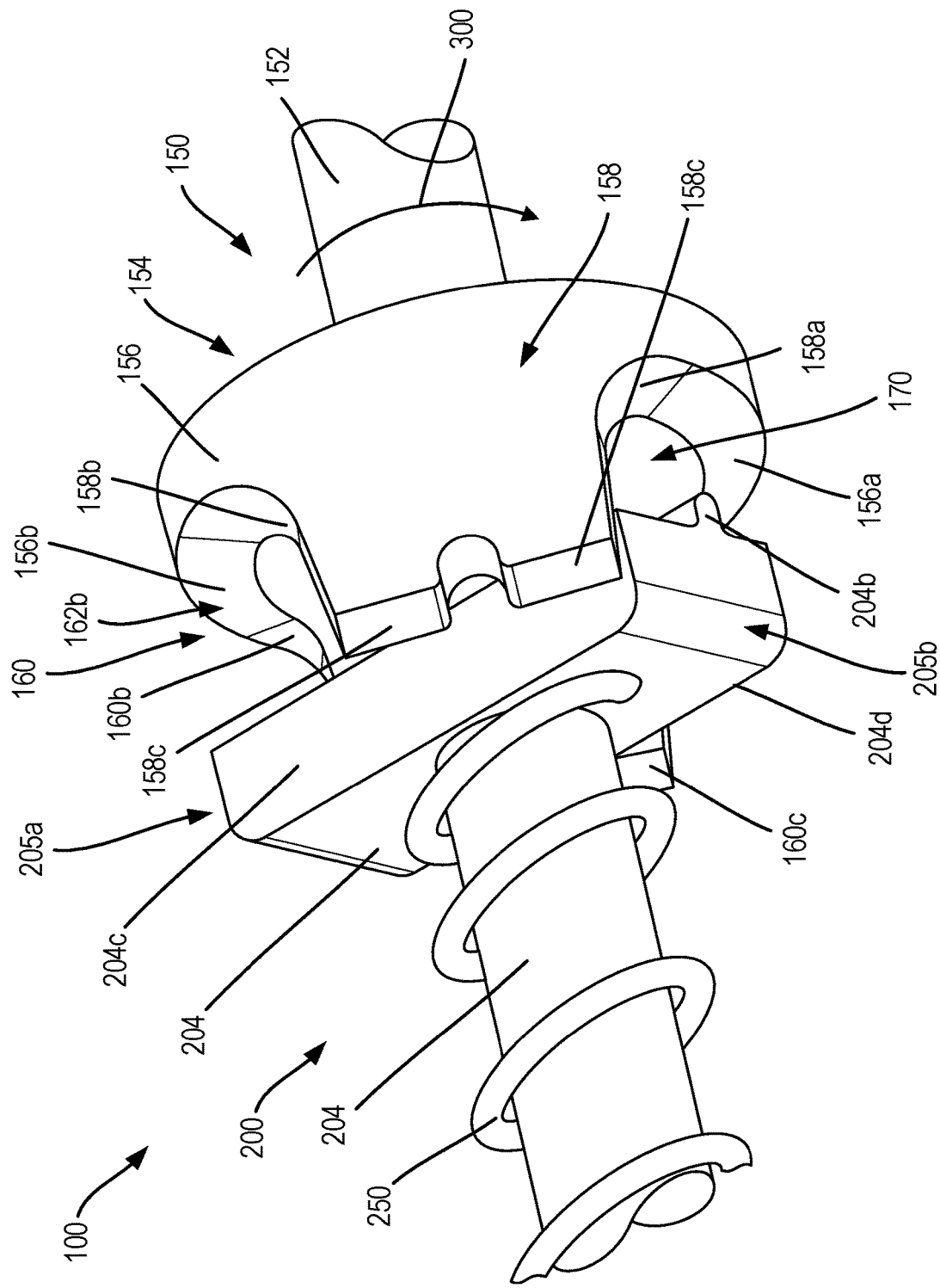
FIG. 13 is the impact mechanism of FIG. 12 with the rotary input camming the rotary output out of the trough, according to at least one aspect of the present disclosure.
Figure 14:
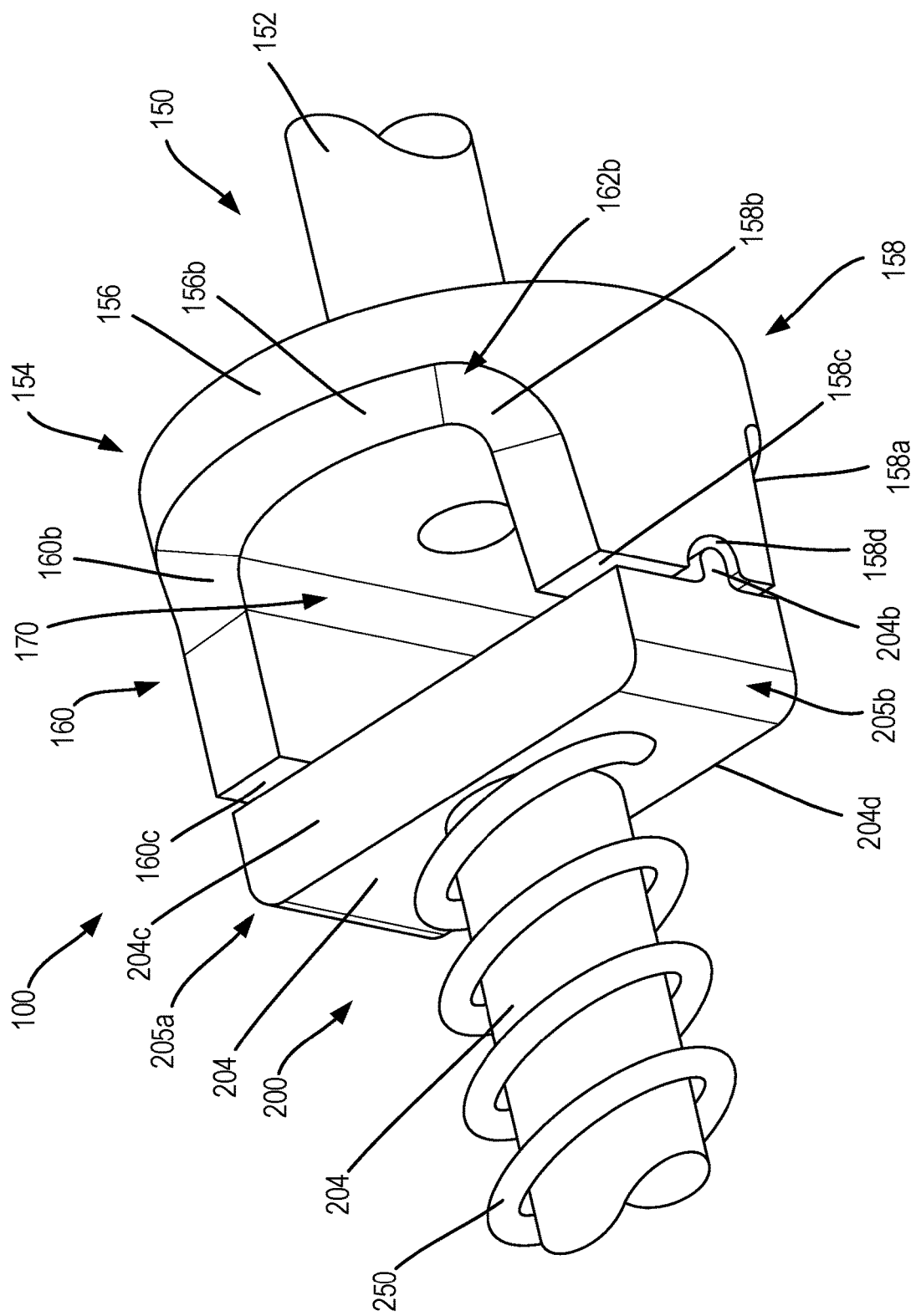
FIG. 14 is the impact mechanism of FIG. 10 returned to the coupled state, according to at least one aspect of the present disclosure.

After the ramped camming surfaces 158*a*, 160*b* impact corresponding impact faces 204*c*, 204*d* of the head 204, further rotation of the rotary input 150 causes the rotary output 200 to be driven out of the trough 170. More specifically, as can be seen in FIG. 13, rotation of the rotary input 150 in the first direction 300 causes the ramped cam 158*a* to engage and cam the impact face 204*c* away from the base 156. Similarly, rotation of the rotary input 150 in the first direction 300 causes the ramped cam 160*b* to engage and cam the impact face 204*d* away from the base 156. The cooperative camming action of the ramped cams 158*a*, 160*b* on the impact faces 204*c*, 204*d* compresses the compression spring 250 and drives the rotary output 200 toward the engaged position. Once the impact faces 204*c*, 204*d* clear the apex of the ramped cam surfaces 158*a*, 160*b*, the rotary input 150 can continue to rotate relative to the rotary output 200 in the first direction 300 until the ridges 204*a*, 204*b* of the head 204 align with the detents 158*d*, 160*d* of the rotary input 150. At such time, the force applied to the head 204 by the compression spring 250 forces the ridges 204*a*, 204*b* into the detents 158*d*, 160*d*, returning the impact mechanism 100 to the coupled state, seen in FIG. 14. It should be noted that, at such time, the ridge 204b is now engaged with 158d and ridge 204a is engaged with detent 160d owing to the relative rotation that occurred between the rotary input 150 and the rotary output 200.

While the above-described process of utilizing the impact mechanism 100 was described with the rotary input 150 rotating in the first direction 300, it should be understood that the process for utilizing the impact mechanism 100 in the second direction 310 would be substantially the same, except that the ramped cam 158b would impact and cam the impact face 204c while the ramped cam 160a would impact and cam the impact face 204d back to the coupled state after the impact mechanism 100 is transitioned to the slipped state. Accordingly, the impact mechanism 100 is able to provide brief peak loads to the rotary output 200 with the rotary input 150 rotating in the first direction 300 and the second direction 310.

In various embodiments, after the rotary input 150 delivers the brief peak load to the rotary output 200 and the impact mechanism 100 is returned to the coupled state, the amount of torque required to rotate the rotary output 200 may still exceed the torque threshold. Accordingly, continued rotation of the rotary input 150 after the ridges 204a, 204b and the detents 158d, 160d have returned to the coupled state can cause the ridges 204a, 204b to "reslip" and repeat the above-referenced impact process of applying a brief peak load to the rotary output 200 again. This allows the impact mechanism 100 to apply multiple successive brief peak loads to overcome the resistance encountered by the rotary output 200.

As described above, the impact mechanism 100 is able to apply brief peak loads that would normally be unavailable by the drive assembly, allowing the drive assembly to drive both high torque functions, such as strong grasping of tissue or performing a staple firing operation, and low torque functions, such as quickly grasping tissue with the jaws of the end effector. Furthermore, the coupling between the ridges 204a, 204b and the detents 158d, 160d eliminates unacceptable grasping backlash when performing the low torque functions.

In various embodiments, a second impact mechanism is contemplated by the present disclosure. The second impact mechanism can be similar in many respects to the impact mechanism 100 except the differences noted hereinbelow. The second impact mechanism can include an impact driver that, unlike impact driver of impact mechanism 100, has four arms rotationally spaced 90° apart from one another relative to a central axis defined by the input shaft 152 that a gap is defined between adjacent arms. Each arm of the impact driver, similar to the arms 158, 160 of the impact mechanism 100, can include a detent and ramped cams on each lateral side thereof. In addition, the second impact mechanism can further include a head that, unlike the "I-shaped" head of the impact mechanism 100, can have a "+ shaped" head, where each of the four arms of the "+ shaped" head includes a ridge extending therefrom that can couple to a corresponding detent in the head of the second impact mechanism. In one aspect, unlike the impact mechanism 100 that has two points of contact between rotary input 150 and the rotary output 200 (ridge 204b with detent 160d and ridge 204a with detent 158d), the second impact mechanism can include four points of contact between the rotary input and the rotary output.

In one aspect, the second impact mechanism can operate in a substantially similar fashion to impact mechanism 100. Unlike the impact mechanism 100, however, the rotary input of the second impact mechanism only rotates 90° relative to the rotary output between coupled states after the second impact mechanism transitions to the slipped state. In one aspect, increasing the points of contact between the rotary input and the rotary output can increase the amount of torque that the rotary input can apply to the rotary output before transitioning to the slipped state. Similarly, increasing the number of arms and impact faces can increase the brief peak load that the rotary input applies to the rotary output in the slipped state.

Various other impact mechanisms are contemplated by the present disclosure. In one aspect, an impact mechanism is contemplated where the rotary output includes detents and the rotary input includes ridges. In one aspect, an impact mechanism is contemplated where the compression spring encircles the shaft of the rotary input and the rotary input is axially movable relative to the rotary output.

As described above, the impact mechanism 100 relies on relative rotation between the rotary input 150 and the rotary output 200 to apply the brief peak loads to the rotary output 200. This relative rotation results in differing amounts of angular rotation of the rotary input 150 and the rotary output 200 while using the impact mechanism 100, such as over the course of a surgical procedure. In one embodiment, referring to FIGS. 10-14, after the impact mechanism 100 transitions to the slipped state and returns to the coupled state, the rotary input 150 of the impact mechanism 100 will have rotated more than the rotary output 200, such as 180° more relative to the rotary output 200. Due to the potential for "slippage" in the impact mechanism 100, a user may have no way of knowing how much rotation from the rotary input 150 has actually been transferred to the rotary output 200. By not knowing how much rotation has actually been transferred to the rotary output 200, the user may inadvertently overclamp or underclamp tissue between the end effector jaws. As another example, by not knowing how much rotation has been transferred to the rotary output 200, the user may inadvertently try to transition the jaws to the open configuration before a staple firing stroke has been completed. As another example, by not knowing how much rotation has been transferred to the rotary output 200, the user may rotate the rotary output 200 too much, resulting in the firing drive jamming into either of the proximal or distal ends of the end effector, potentially damaging the end effector. Accordingly, a control system for determining how much angular rotation has been transferred to the rotary output 200 from the rotary input 150 is desired.

Figure 15:
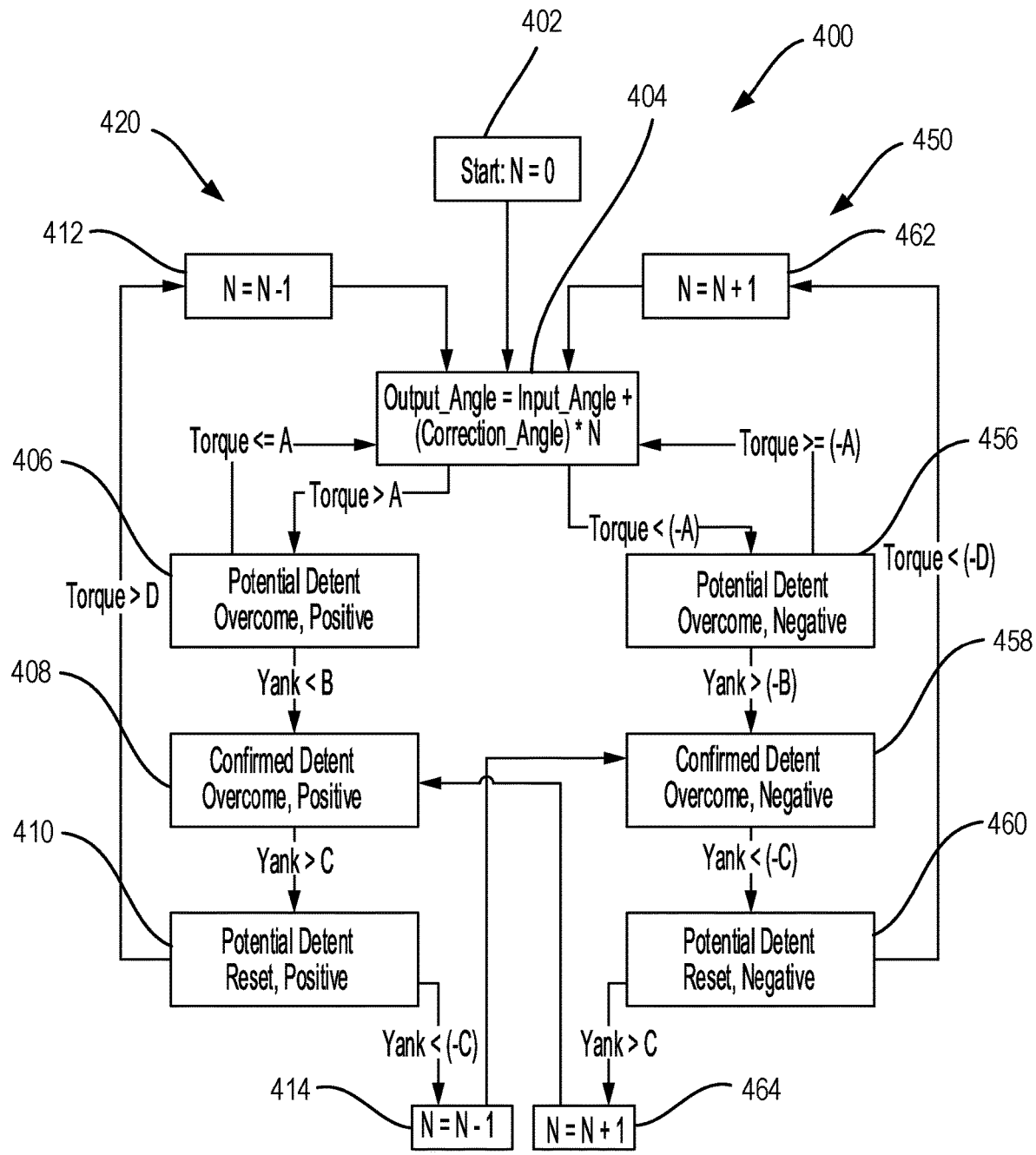
FIG. 15 is an algorithm for determining the output angle of the rotary output of an impact mechanism, according to at least one aspect of the present disclosure.

Referring now to FIG. 15, an algorithm 400 for determining the output angle of the rotary output 200 of the impact mechanism 100 is provided, according to at least one aspect of the present disclosure. In one aspect, the algorithm 400 can determine the angle of the rotary output 200 by monitoring the number of slippages in the impact mechanism 100, i.e., the number of times the impact mechanism 100 transitions to the slipped state and then back to the coupled state. As will be explained in more detail below, the occurrence of a slippage can be used with a predetermined correction angle and the angle of the rotary input 150 to determine the angle of the rotary output 200, and therefore, determine how much angular rotation has been transferred to the rotary output 200 by the rotary input 150. In various embodiments, the algorithm 400 can be stored in a memory and be executed by any suitable means, such as with a controller, a control system, a control circuit, a processor, or any other suitable manner for carrying out algorithms as are known in the art or described elsewhere herein.

As referenced above, the algorithm 400 can determine the output angle of the rotary output 200 using, among other things, a predetermined correction angle. In one aspect, the correction angle is defined as the angular rotation of the rotary input 150 relative to the rotary output 200 between the coupled states of the impact mechanism after transitioning to the slipped state. In various embodiments, the correction angle is based on the geometric relationship between the rotary input 150 and the rotary output 200 and the number of points of contact between the same. In one embodiment, due to the geometric relationship of the rotary output 200 and the rotary input 150 of the impact mechanism 100, as seen in FIGS. 10-14, the rotary input 150 rotates 180° relative to the rotary output 200 between transitioning to the slipped state and then returning to the coupled state. In another embodiment, due to the geometric relationship of the rotary output and the rotary input of the second impact mechanism, described above, the rotary input rotates 90° relative to the rotary output between transitioning to the slipped state and then returning to the coupled state. Accordingly, the correction angle can be defined based on how far the rotary input will rotate relative to the rotary output between each slippage and recoupling of the respective impact mechanism. In various embodiments, the correction angle can be greater than 180°, such as 270° or 360°. In various embodiments, the correction angle can be less than 90°, such as 45°. In various embodiments, the correction angle can be between 90° and 180°, such as 135°. Any suitable impact mechanism can be constructed such that a desired correction angle can be achieved.

As referenced above, the algorithm 400 can carried out by, among other things, a control system. At the outset of using the impact mechanism 100, the control system can initiate the algorithm 400 to set a slip count at block 402, which can updated over the course of operation of the impact mechanism 100, as will be described below. In one aspect, the control system can initially set the slip count N to 0, indicating that the angle of the rotary input 150 is the same as the angle of the rotary output 200, i.e., not offset, as determined by the equation at block 404.

In addition, the control system can set the correction angle of the impact mechanism to be used for determining the output angle of the rotary output 200. In one aspect, the correction angle can be set by a user at a user interface, according to the known geometric relationship between the rotary input and the rotary output. In one aspect, the correction angle can be automatically set by the control system. In one embodiment, the control system can include an RFID scanner than can interrogate an RFID tag on one or both of the rotary input and/or rotary output to determine the type of rotary input and rotary output being used in the impact mechanism. Based on the reading(s), the control system can determine the geometric relationship between the rotary input and the rotary output to determine the correction angle of the impact mechanism based on data stored in a memory or obtained from a cloud-based system. In various other embodiments, the control system can set a default correction angle, such as 180°, to be applied unless an input is received from a user indicating otherwise. In various embodiments, the control system can prompt a user to provide an input, such as the type impact mechanism being used, the surgical instrument being used, or a numerical value associated with the surgical instrument, such as a serial number or model number, such that the control system can determine the impact mechanism that is to be used based on data stored in a memory or obtained from a cloud-based server. Various other means for determining the correction angle are contemplated by the present disclosure.

As referenced above, the control system can determine the output angle of the rotary output 200 according to, among other things, the input angle of the rotary input 150. In one aspect, the angle of the rotary input can be sensed and/or tracked by the control system in any suitable manner, such as with an angular sensor, an encoder, an optical-based angular measuring system, or any suitable mechanism for tracking the angle of the rotary input 150, such as those disclosed elsewhere herein. As can be seen at block 404, the control system can calculate the output angle by adjusting the determined input angle of the rotary input with the product of the correction angle and the slip count N. For instance, at the outset of using the impact mechanism where the slip count N is 0, the output angle of the rotary output will be equal to the input angle of the rotary input.

In various embodiments, the control system can monitor various parameters of the impact mechanism 100 in order to adjust the slip count N. In operation, as discussed above, the rotary input 150 can rotate in a first direction 300, such as a clockwise direction, or a second direction 310, such as a counterclockwise direction, to transfer corresponding rotational motion to the rotary output 200 in a first direction 302 or a second direction 312, respectively. Accordingly, owing to the two directional rotation of the rotary input 150, the impact mechanism 100 can experience two types of slippage events—a first slippage event, where the rotary input 150 slips and recouples while rotating in the first direction 300, such as is seen in the progression of FIGS. 10-14, and a second slippage event, where the rotary input 150 slips and recouples while rotating in the second direction 310. Accordingly, the algorithm 400 can adjust the slip count N based on which slippage event is detected. In one aspect, the control system can determine the occurrence of a first slippage event and decrement the slip count at blocks 412 or block 414 by determining if certain conditions are satisfied along a first path 420 of the algorithm 400, as will be described in more detail below. In another aspect, the control system can determine the occurrence of a second slippage event and increment the slip count at block 462 or block 464 by determining if certain conditions are satisfied along a second path 450 of the algorithm 400, as will be described in more detail below.

In one aspect, the impact mechanism 100 can begin in the coupled state, such that rotation of the rotary input 150 in a first direction 300 causes a corresponding rotation in the rotary output 200 in a first direction 302. During the operation of the impact mechanism 100, the control system can monitor the input torque that the rotary input 150 applies to the rotary output 200 (via the coupled ridges 204a, 204b and detents 158d, 160d, as an example). In various embodiments, the control system can monitor the input torque using any suitable torque or force sensor. In one aspect, the control system can monitor the input torque using a strain-gauge situated on the rotary input 150 and/or the rotary output 200. In various embodiments, the control system can monitor the input torque by monitoring an amount of current or voltage that is supplied to the motor that drives the rotary input 150, such as with a current or voltage sensor, respectively. Various other mechanisms for monitoring the input torque provided by the rotary input 150 are contemplated by the present disclosure, such as those disclosed elsewhere herein.

As referenced above, when the rotary output 200 encounters resistance, due to, for example, thick tissue being positioned between the jaws of the end effector, the amount of torque required to rotate the rotary output 200 increases.

The control system can monitor the input torque applied by the rotary input 150 and compare the monitored torque against torque thresholds A and −A. In various embodiments, the torque thresholds A and −A can be stored in a memory or in a cloud-based system and can be retrieved by the control system. In various embodiments, the torque thresholds A and −A can be thresholds that are indicative of the rotary input 150 applying a torque to the rotary output 200 that causes compression spring 250 to compress and thus, potentially results in the ridges 204a, 204b slipping from the detents 158d, 160d. In various embodiments, the magnitudes of the torque thresholds A and −A can be the same, only mirrored along the x-axis, i.e., they differ by a factor of −1. In various other embodiments, the magnitude of the torque threshold A can be different than the torque threshold −A. In various embodiment, rotation of the rotary input 150 in the first direction causes the control system to sense a positive torque value and rotation of the rotary input 150 in the second direction causes the control system to sense a negative torque value.

In one aspect, detection of the input torque reaching or exceeding the torque threshold A can be indicative of a slippage event where the rotary input 150 slips relative to the rotary output 200 while rotating in a first direction, such as the first direction 300. Similarly, in one aspect, detection of the input torque reaching or dropped below the torque threshold −A can be indicative of a slippage event where the rotary input 150 slips relative to the rotary output 200 while rotating in a second direction, such as the second direction 310. Based on the above-described threshold detection, the control system can proceed along a first path 420 of the algorithm 400, indicative of a potential occurrence of a slippage event in the first direction when the torque threshold A is reached or exceeded, or a second path 450 of the algorithm 400, indicative of a potential occurrence of a slippage event in the second direction when the torque threshold −A is reached or dropped below.

In one aspect, when the control system detects that the torque threshold A has been reached or exceeded, the control system can proceed to block 406, indicating that the ridges 204a, 204b of the rotary output 200 may have potentially slipped from the detents 158d, 160d of the rotary input 150 while the rotary input 150 was rotating in the first direction. At block 406, the control system can verify the occurrence of the slippage event, i.e., determining if the ridges 204a, 204b actually slipped from the detents 158d, 160d, by comparing a determine yank associated with the impact mechanism 100 against a yank threshold B. In one aspect, yank is defined as the derivative of torque applied by the rotary input 150 over time.

In the event that the ridges 204a, 204b actually slipped from the detents 158d, 160d, as referenced above, the impact mechanism 100 will transition to the slipped state, such that the rotary input 150 will rotate relative to the rotary output 200. At such time, since the ridges 204a, 204b will have drivingly decoupled from the detents 158d, 160d, the amount of torque the rotary input 150 applies to the rotary output 200 will quickly drop to zero, resulting in a yank with a negative slope that drops below the yank threshold B. In various embodiments, the yank threshold B can be stored in a memory or in a cloud-based system and can be retrieved by the control system. In various embodiments, the yank threshold B can be based on known properties of the impact mechanism. In various embodiments, the yank threshold B can be a threshold value indicative of the ridges 204a, 204b drivingly decoupling from the detents 158d, 160d.

Upon the control system detecting the occurrence of the yank dropping below the yank threshold B at block 406, the control system can confirm that a slippage event in the first direction has actually occurred and proceed to block 408. In the event that the ridges 204a, 204b didn't actually slip from the detents 158d, 160d, rotation of the rotary input 150 will continue to cause corresponding rotation of the rotary output 200. In such an instance, the control system can detect that the input torque provided by the rotary input 150 drops below the torque threshold A and proceed back to block 404 to continue to monitor the input torque of the rotary input 150 against torque thresholds A, −A. In some embodiments, at block 406, the control system can determine that a slippage event did not actually occur by determining if the detected yank is greater than the yank threshold B, which can be indicative of a slippage event not actually occurring.

As referenced above, once the control system has determined that the impact mechanism 100 has transitioned to the slipped state and that the rotary input 150 is now rotating relative to the rotary output 200, the control system proceeds to block 408. At block 408, the control system can monitor for when the rotary input 150 and rotary output 200 have returned to the coupled state. At block 408, the control system can monitor for the occurrence of a yank of the impact mechanism 100 reaching or exceeding a yank threshold C, which can be indicative of the rotary input 150 impacting the rotary output 200 to deliver the brief peak load and the impact mechanism 100 potentially returning to the coupled state. In the event the control system detects the occurrence of the yank exceeding the yank threshold C, the control circuit can proceed to block 410 to verify if the rotary input 150 and the rotary output 200 have actually returned to the coupled state. In various embodiments, the yank threshold C can be stored in a memory or in a cloud-based system and can be retrieved by the control system. In various embodiments, the yank threshold C can be based on known properties of the impact mechanism. In various embodiments, the, the yank threshold C can be a threshold value indicative of the ridges 204a, 204b potentially drivingly recoupling with the detents 158d, 160d.

At block 410, the control system can verify if the rotary input 150 and the rotary output 200 have returned to the coupled state by determining if the input torque applied by the rotary input 150 exceeds a torque threshold D, which is indicative of the rotary input 150 and the rotary output 200 returning to the coupled state. In various embodiments, the torque threshold D can be stored in a memory or in a cloud-based system and can be retrieved by the control system. In various embodiments, the torque threshold D can be based on known properties of the impact mechanism. In various embodiments, the torque threshold D can be a known torque threshold that is indicative of the impact mechanism reaching the coupled state. In various embodiments, the torque threshold D can be a threshold value indicative of the ridges 204a, 204b drivingly recoupling with the detents 158d, 160d.

At block 410, if the control system does not detect the input torque from the rotary input 150 reaching or exceeding the torque threshold D, the control system can also determine if the detected yank drops below a yank threshold −C. In various embodiments, detection of a yank below yank threshold −C is indicative of the rotary input 150 and the rotary output 200 returning to the coupled state, then the rotary input 150 proceeding to rotate in the opposite direction, such as the second direction 310, and slipping in the second direction. In various embodiments, detection of a yank below yank threshold −C is indicative of the rotary input 150 and the rotary output 200 not returning to the coupled state, but rather, the rotary input 150 rotating in the opposite direction, i.e., the second direction, before the impact mechanism 100 returned to the coupled state. In various embodiments, the yank threshold −C can be stored in a memory or in a cloud-based system and can be retrieved by the control system. In various embodiments, the yank threshold −C can be based on known properties of the impact mechanism. In various embodiments, the yank threshold −C can be a known threshold that is indicative of the impact mechanism reaching the coupled state and then rotating and slipping in the second direction. In various embodiments, the yank threshold −C can be a known threshold that is indicative of the impact mechanism rotating in the second direction prior to reaching the coupled state. In various embodiments, the magnitude of the yank threshold −C can be the same as yank threshold C, only mirrored along the x-axis, i.e., they differ by a factor of −1. In various other embodiments, the magnitude of the yank threshold −C can be different than the yank threshold C. In various embodiments, the yank threshold −C can be the same as yank threshold B. In various embodiments, the yank threshold −C can be different than yank threshold B.

In either above-described scenario (torque reaching or exceeding torque threshold D or yank reaching or dropping below −C), the control system can decrement the slip count by one at block 412 or block 414, depending on which above-described scenario was satisfied and detected by the control system.

In one embodiment, in the event that the rotary input 150 of impact mechanism 100 slipped from the rotary output 200 and returned to the coupled state along block 412, the control system can then determine the output angle of the rotary output 200 relative to the rotary input 150 at block 404. As referenced above, at block 404, the correction angle for impact mechanism 100 is predetermined (180°) and known. In addition, owing to the slip count beginning at zero and then decrementing at block 412, the slip count is known by the control system to be −1 (or one less than the previous slip count N in a scenario where the slip count had previously experienced a slippage event). Based on this data, the control system can determine that the output angle of the rotary output 200 is equal to the input angle of the rotary input 150 minus 180°, i.e. the rotary output 200 is offset from the rotary input 150 by 180° in the second direction as the rotary input 150 rotated 180° more in the first direction.

Accordingly, the control system can utilize this corrected output angle of the rotary output 200 to ensure that a correct amount of input rotary motions are applied to the rotary input 150 to perform a particular end effector function. In one aspect, when performing a certain function, the control system can know that the rotary input 150 will need to rotate the rotary output 200, at least, an additional 180° in the first direction with the rotary input 150. In various embodiments, the control system can communicate a signal to a display such that a user is provided real-time data regarding how many slippage events occur at the impact mechanism 100 and how much rotation has been transferred to the rotary output 200. Based on this information, a user may see that the impact mechanism 100 is encountering more slippages than expected, which could be indicative of too much tissue being positioned in the end effector. Accordingly, a user can decide to retract the firing mechanism and reposition the end effector in a new location.

In another aspect, the impact mechanism 100 can begin in the coupled state, such that rotation of the rotary input 150 in a second direction 310 causes a corresponding rotation in the rotary output 200 in a second direction 312. During the operation of the impact mechanism 100, the control system can monitor the input torque that the rotary input 150 applies to the rotary output 200 (via the coupled ridges 204a, 204b and detents 158d, 160d).

As referenced above, when the rotary output 200 encounters resistance, due to, for example, thick tissue being positioned between the jaws of the end effector, the amount of torque required to rotate the rotary output 200 increases. The control system can monitor the input torque applied by the rotary input and compare the monitored torque against torque thresholds A and −A. In one aspect, detection of the input torque reaching or dropping below the torque threshold −A can be indicative of a slippage event where the rotary input 150 slips relative to the rotary output 200 while rotating in a second direction, such as the second direction 310. Based on this threshold detection, the control system can proceed along a second path 450 of the algorithm 400, indicative of a potential occurrence of a slippage event in the second direction.

In one aspect, when the control system detects that the torque threshold −A has been reached or dropped below, the control system can proceed to block 456, indicating that the ridges 204a, 204b of the rotary output 200 have potentially slipped from the detents 158d, 160d of the rotary input 150 while the rotary input 150 was rotating in the second direction. At block 456, the control system can next verify the occurrence of the slippage event, i.e., determining if the ridges 204a, 204b actually slipped from the detents 158d, 160d, by comparing a determine yank associated with the impact mechanism 100 against a yank threshold −B.

In the event that the ridges 204a, 204b actually slipped from the detents 158d, 160d, as referenced above, the impact mechanism 100 will transition to the slipped state, such that the rotary input 150 will rotate relative to the rotary output 200. At such time, since the ridges 204a, 204b will have drivingly decoupled from the detents 158d, 160d, the amount of torque the rotary input 150 applies to the rotary output will quickly drop to zero, resulting in a yank with a positive slope that reaches or exceeds the yank threshold −B. In various embodiments, the magnitude of the yank threshold −B can be the same as yank threshold B, only mirrored along the x-axis, i.e., they differ by a factor of −1. In various other embodiments, the magnitude of the yank threshold −B can be different than the yank threshold B. In various embodiments, the yank threshold −B can be stored in a memory or in a cloud-based system and can be retrieved by the control system. In various embodiments, the yank threshold −B can be based on known properties of the impact mechanism. In various embodiments, the yank threshold −B be a threshold value indicative of the ridges 204a, 204b drivingly decoupling from the detents 158d, 160d. In various embodiments, the yank threshold −B can be the same as yank threshold C. In various embodiments, the yank threshold −B can be different than yank threshold C.

Upon the control system detecting the occurrence of the yank reaching or exceeding the yank threshold −B at block 456, the control system can confirm that a slippage event in the second direction has actually occurred and proceed to block 458. In the event that the ridges 204a, 204b didn't actually slip from the detents 158d, 160d, rotation of the rotary input 150 will continue to cause corresponding rotation of the rotary output 200. In such an event, the control system can detect that the input torque provided by the rotary input 150 reaches or exceeds the torque threshold −A and proceed back to block 404 to continue to monitor the input torque of the rotary input 150 against torque thresholds A, −A. In some embodiments, at block 456, the control system can determine that a slippage event did not actually occur by determining if the detected yank is less than the yank threshold −B, which can be indicative of a slippage event not actually occurring.

As referenced above, once the control system has determined that the impact mechanism 100 has transitioned to the slipped state and that the rotary input 150 is now rotating relative to the rotary output 200, the control system proceeds to block 458. At block 458, the control system can monitor for when the rotary input 150 and rotary output 200 have returned to the coupled state. At block 458, the control system can monitor for the occurrence of yank reaching or dropping below a yank threshold −C, which can be indicative of the rotary input 150 impacting the rotary output 200 to deliver the brief peak load and the impact mechanism potentially returning to the coupled state. In the event the control system detects the occurrence of yank reaching or dropping below the yank threshold −C, the control circuit can proceed to block 460 to verify if the rotary input 150 and the rotary output 200 have actually returned to the coupled state.

In various embodiments, the magnitude of the yank threshold −C can be the same as yank threshold C, only mirrored along the x-axis, i.e., they differ by a factor of −1. In various other embodiments, the magnitude of the yank threshold −C can be different than the yank threshold C. In various embodiments, the yank threshold −C can be stored in a memory or in a cloud-based system and can be retrieved by the control system. In various embodiments, the yank threshold −C can be based on known properties of the impact mechanism. In various embodiments, the yank threshold −C be a threshold indicative of the ridges 204*a*, 204*b* potentially drivingly recoupling with the detents 158*d*, 160*d*.

At block 460, the control system can verify if the rotary input 150 and the rotary output 200 have returned to the coupled state by determining if the input torque applied by the rotary input 150 reaches or drops below a torque threshold −D, which is indicative of the rotary input 150 and the rotary output 200 returning to the coupled state. In various embodiments, the magnitude of the torque threshold −D can be the same as torque threshold D, only mirrored along the x-axis, i.e., they differ by a factor of −1. In various other embodiments, the magnitude of the torque threshold −D can be different than the torque threshold D. In various embodiments, the torque threshold −D can be stored in a memory or in a cloud-based system and can be retrieved by the control system. In various embodiments, the torque threshold −D can be based on known properties of the impact mechanism. In various embodiments, the torque threshold −D can be a known torque threshold that is indicative of the impact mechanism actually reaching the coupled state.

At block 460, if the control system does not detect the input torque from the rotary input 150 reaching or dropping below the torque threshold −D, the control system can determine if the detected yank reaches or exceeds the yank threshold C. In various embodiments, detection of a yank reaching or exceeding yank threshold C is indicative of the rotary input 150 and the rotary output 200 returning to the coupled state, then the rotary input 150 proceeding to rotate in the opposite direction, such as the first direction 310, and slipping in the first direction. In various embodiments, detection of a yank reaching or exceeding yank threshold C is indicative of the rotary input 150 and the rotary output 200 not returning to the coupled state, but rather, the rotary input 150 rotating in the opposite direction, i.e., the first direction, before the impact mechanism 100 returned to the coupled state. In either of the above-described scenarios (torque reaching or dropping below −D or yank reaching or exceeding C), the control system can increment the slip count by one at block 462 or block 464, depending on which scenario referenced above has been satisfied and detected by the control system.

In one embodiment, in the event that the rotary input 150 of impact mechanism 100 slipped from the rotary output 200 and returned to the coupled state along block 462, the control system can then determine the output angle of the rotary output 200 relative to the rotary input 150 at block 404. As referenced above, at block 404, the correction angle is predetermined (180°) and known. In addition, owing to the slip count beginning at zero and then incrementing at block 462, the slip count is known by the control system to be 1 (or one more than the previous slip count N in a scenario where the slip count had previously experienced a slippage event). With this data, the control system can determine that the output angle of the rotary output 200 is equal to the input angle of the rotary input 150 plus 180°, i.e. the rotary output 200 is offset from the rotary input 150 by 180° in the first direction as the rotary input 150 rotated 180° more in the second direction. The control system can utilize this corrected output angle of the rotary output 200 to ensure that a correct amount of input rotary motions are applied to the rotary input 150 to perform a particular end effector function. In one aspect, when performing a certain function, the control system can know that the rotary input 150 will need to rotate the rotary output 200, at least, an additional 180° in the second direction.

As referenced above, at blocks 410 and 460, in the event that a respectively torque threshold D, −D is not reached or eclipsed, the control system can determine that the rotary input 150 has begun to rotate in an opposite direction. Accordingly, the control system can proceed to an opposite path of the algorithm 400 that it was previously following. In one embodiment, as can be seen in FIG. 15, when the rotary input 150 experienced a slippage event when rotating in the first direction, the control system proceeds along the first path 420. However, at block 410, when the yank is detected to be below yank threshold −C, the control system can decrement the slip count at block 414 and then proceed to block 458, which is part of the second path 450 of the algorithm 400 indicative of a potential slippage event in the second direction.

Similarly, in one embodiment, as can be seen in FIG. 15, when the rotary input 150 experienced a slippage event when rotating in the second direction, the control system proceeds along the second path 450. However, at block 460, when the yank is detected to be above yank threshold C, the control system can increment the slip count at block 464 and then proceed to block 408, which is part of the first path 420 of the algorithm 400 indicative of a potential slippage event in the first direction. Accordingly, the control system, using algorithm 400, is able to account for slippage events when the rotary input 150 changes rotational directions during use.

Figure 16:
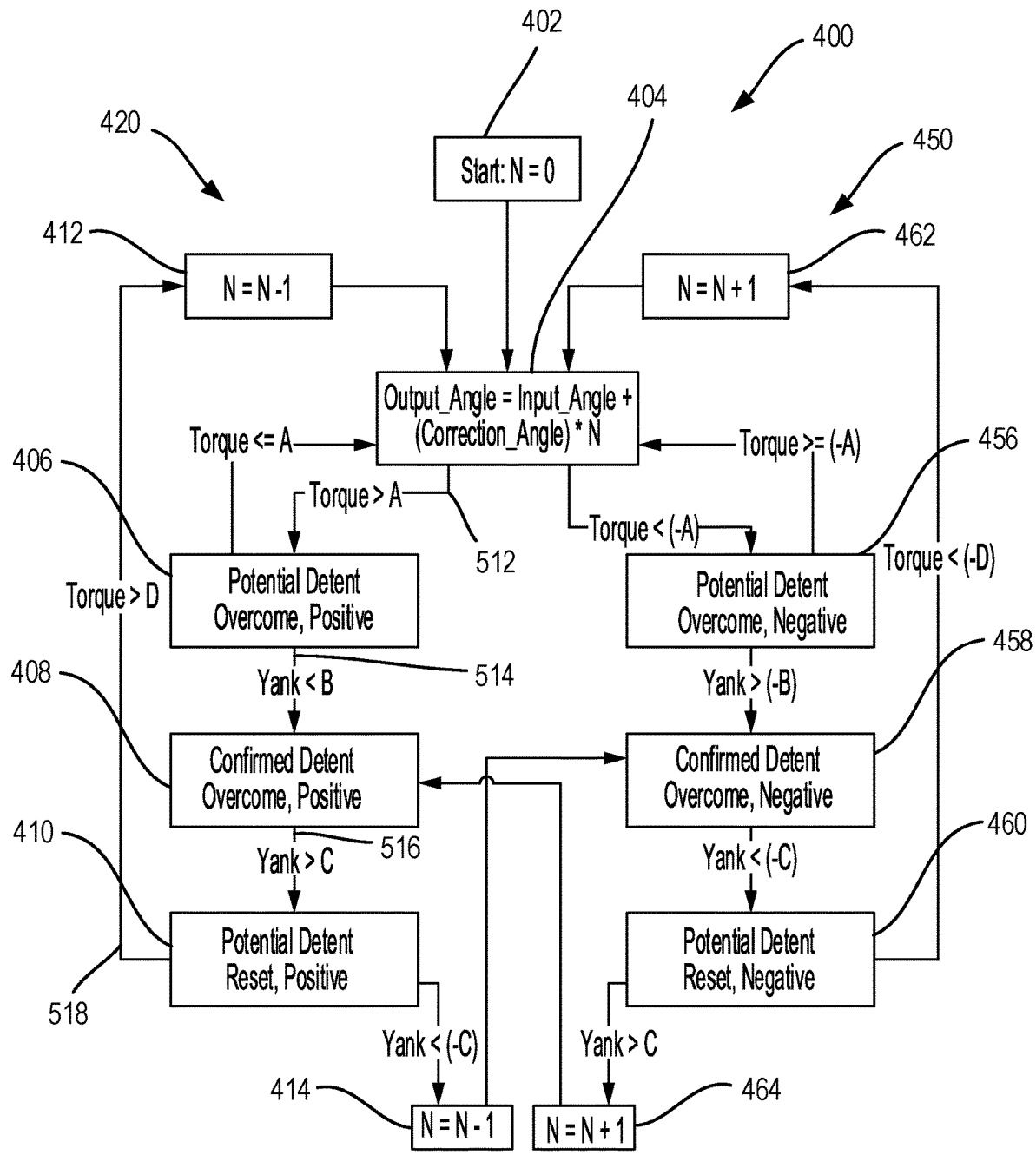
FIGS. 16-18 is a first example implementation of the algorithm of FIG. 15, according to at least one aspect of the present disclosure.
Figure 17:
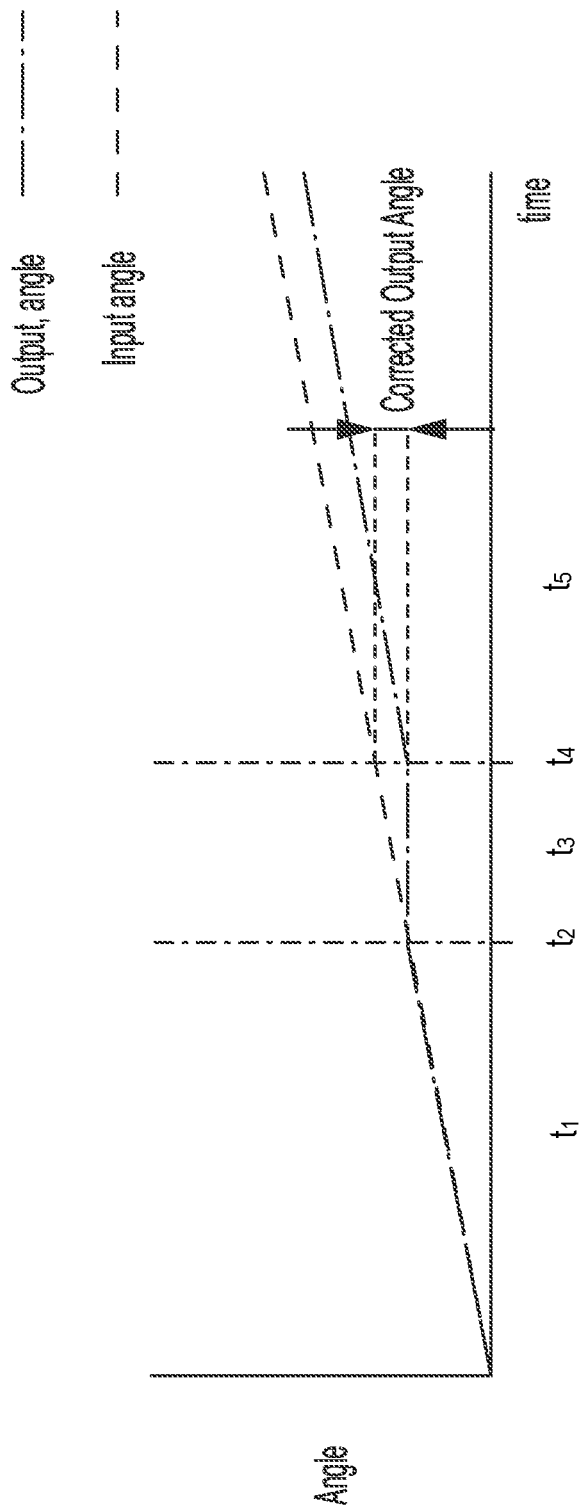
Figure 18:
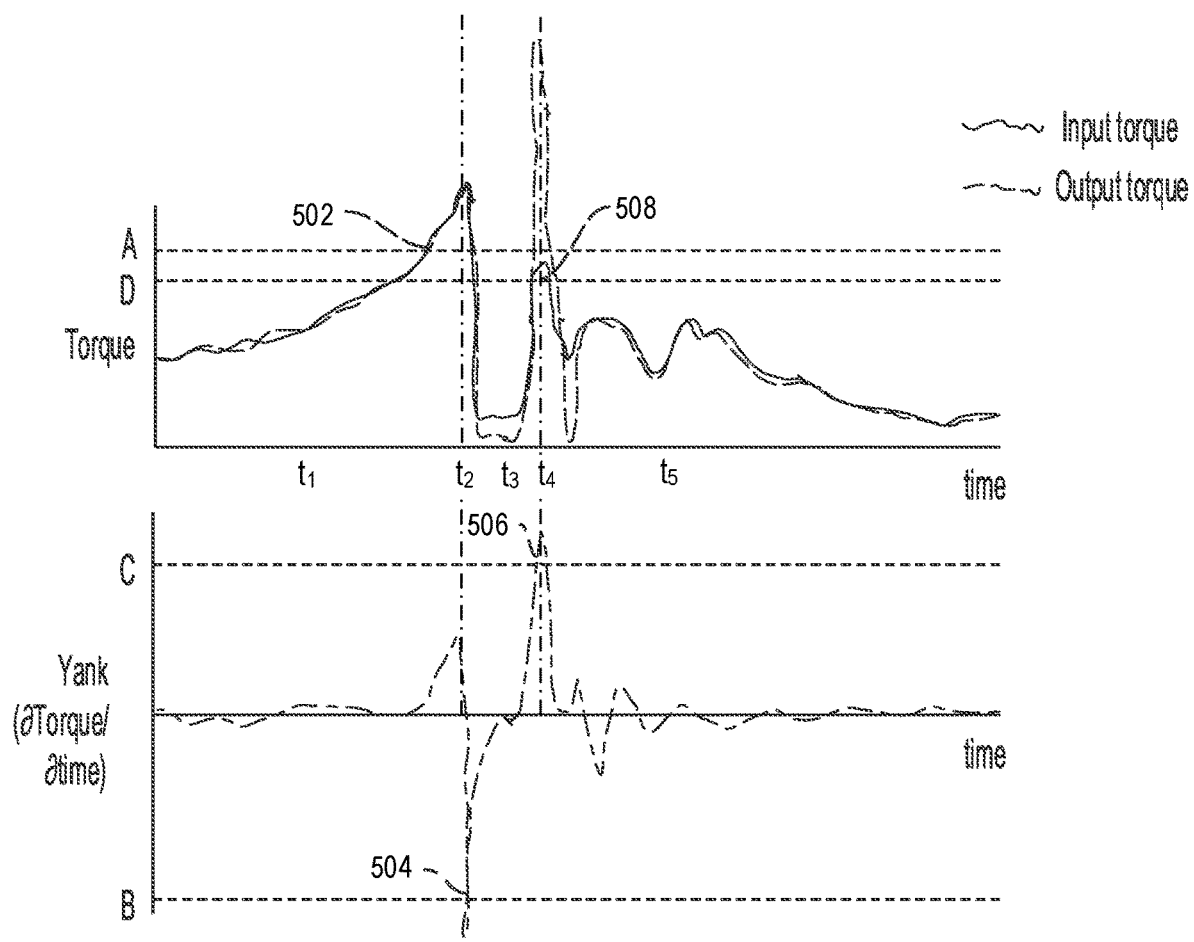

Referring now to FIGS. 16-18, a first example implementation of the impact mechanism 100 using algorithm 400 is provided, according to at least one aspect of the present disclosure. As can be in FIG. 17, for $t_1$, the rotary input 150 and the rotary output 200 are in a coupled state such that the input angle and the output angle are identical, and thus, overlap, while the rotary input 150 is rotated by, for example, a motor. As can be in FIG. 18, during $t_1$, the rotary output 200 begins to experience resistance, causing the input torque provided by the rotary input 150 to increase. At $t_2$, the input torque exceeds 502 torque threshold A, indicating that a potential slippage event has occurred. Accordingly, upon detection of the torque threshold A being exceeded, the control system proceeds 512 from block 404 to block 406 to verify if a slippage event actually occurred. As can be seen in FIG. 18, the control system determines that the yank of the impact mechanism 100 has dropped below 504 yank threshold C, confirming that a slippage event in the first direction has actually occurred. Accordingly, the control system proceeds 514 from block 406 to block 408 to monitor for the rotary input 150 and the rotary output 200 returning to the coupled state.

As can be seen in FIG. 18, during $t_3$, since the rotary input 150 is rotating relative to the rotary output 200, no torque is being transferred to the rotary output 200. At $t_4$, the control system detects a yank that exceeds 506 the yank threshold C, which is indicative of the impact mechanism 100 potentially returning to the coupled state. Accordingly, the control system proceeds 516 from block 408 to block 410 to determine if the impact mechanism actually returned to the coupled state. At $t_4$, the control system detects an input torque from the rotary input 150 that exceeds 508 torque threshold D, which is indicative of the impact mechanism 100 actually returning to the coupled state. As can be seen in FIG. 18, at $t_4$, the output torque from the rotary out 200 spikes as a result of the impact received from the rotary input 150, i.e., the rotary input 150 delivers a brief peak load to the rotary output 200. Due to the control system detecting the input torque from the rotary input 150 exceeding torque threshold D, the control system proceeds 518 to block 412 and decrements the slip count N by one. The control system can then utilize the known correction angle, known angular data out the rotary input (acquired, for example, from an angular sensor), and the updated slip count to adjust the output angle of the rotary output 200, as can be seen in FIG. 17. Accordingly, the algorithm 400 tracks the angular difference between the rotary input 150 and rotary output 200 over the course of using the impact mechanism 100.

Figure 19:
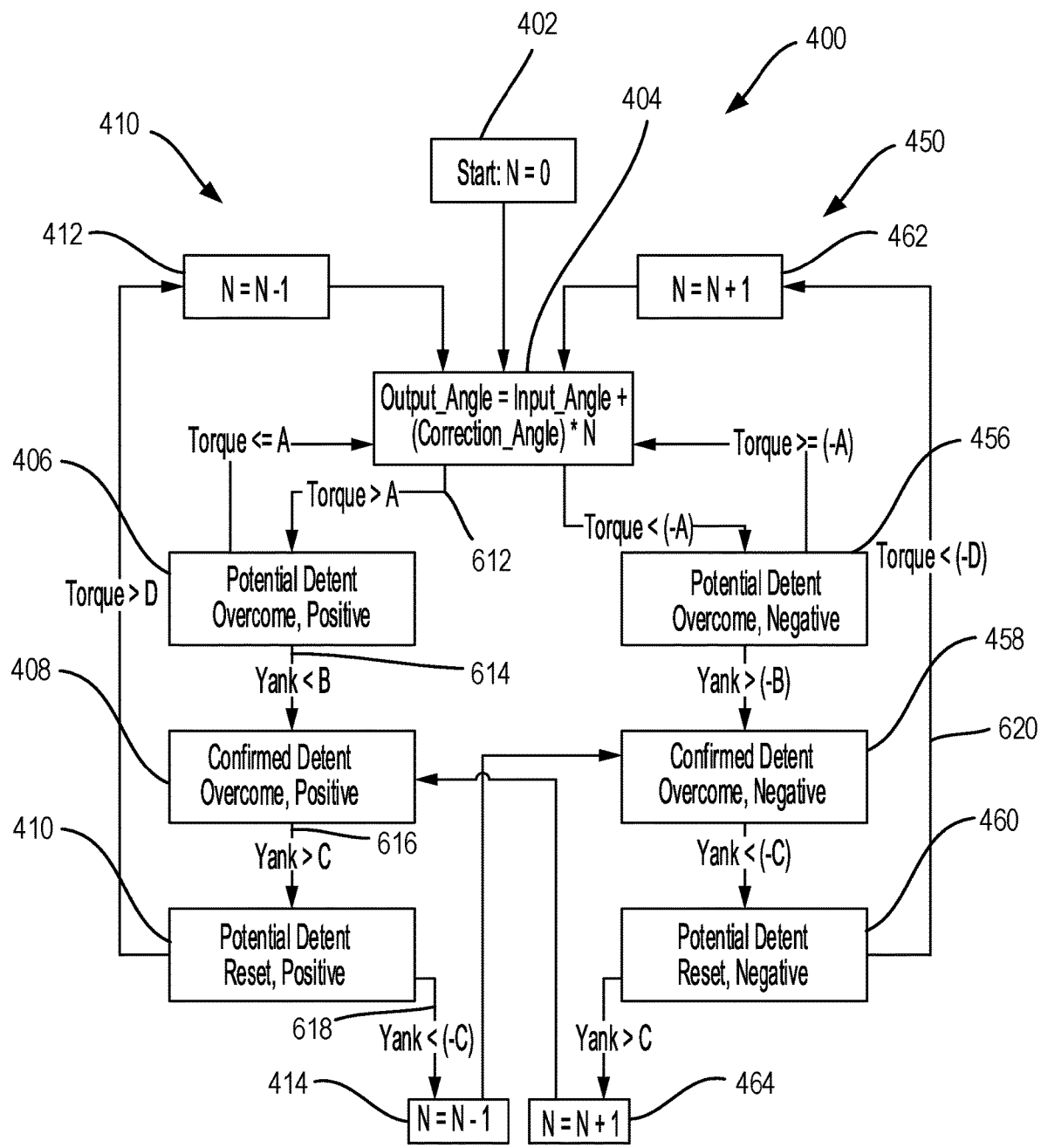
FIGS. 19-21 is a second example implementation of the algorithm of FIG. 15, according to at least one aspect of the present disclosure.
Figure 20:
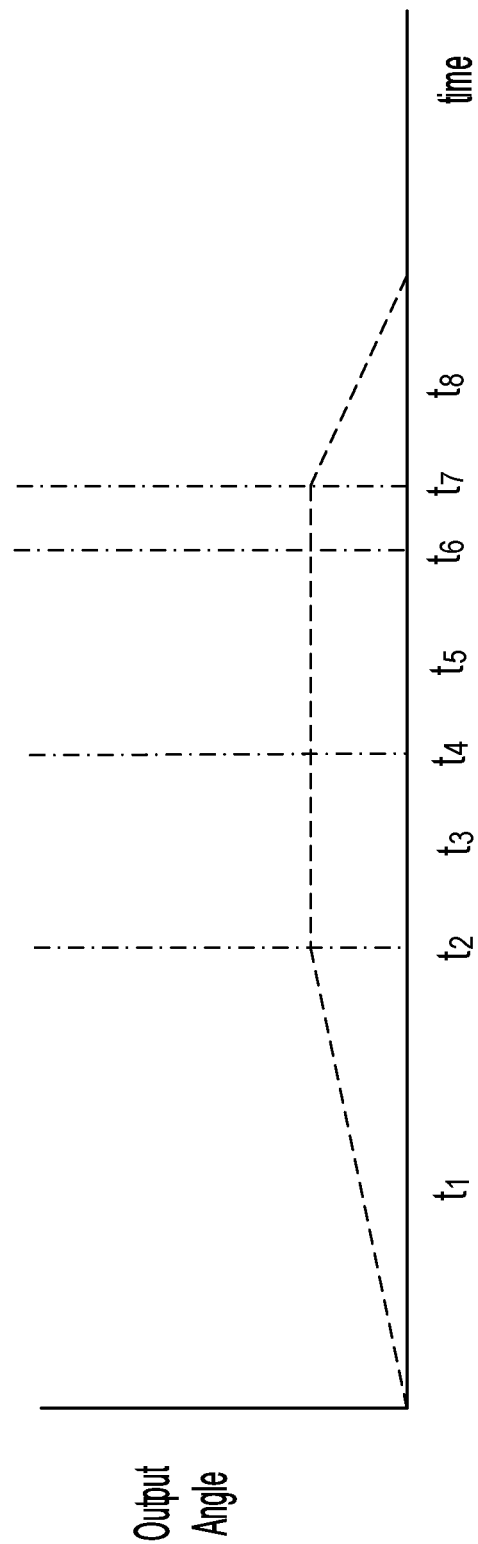
Figure 21:
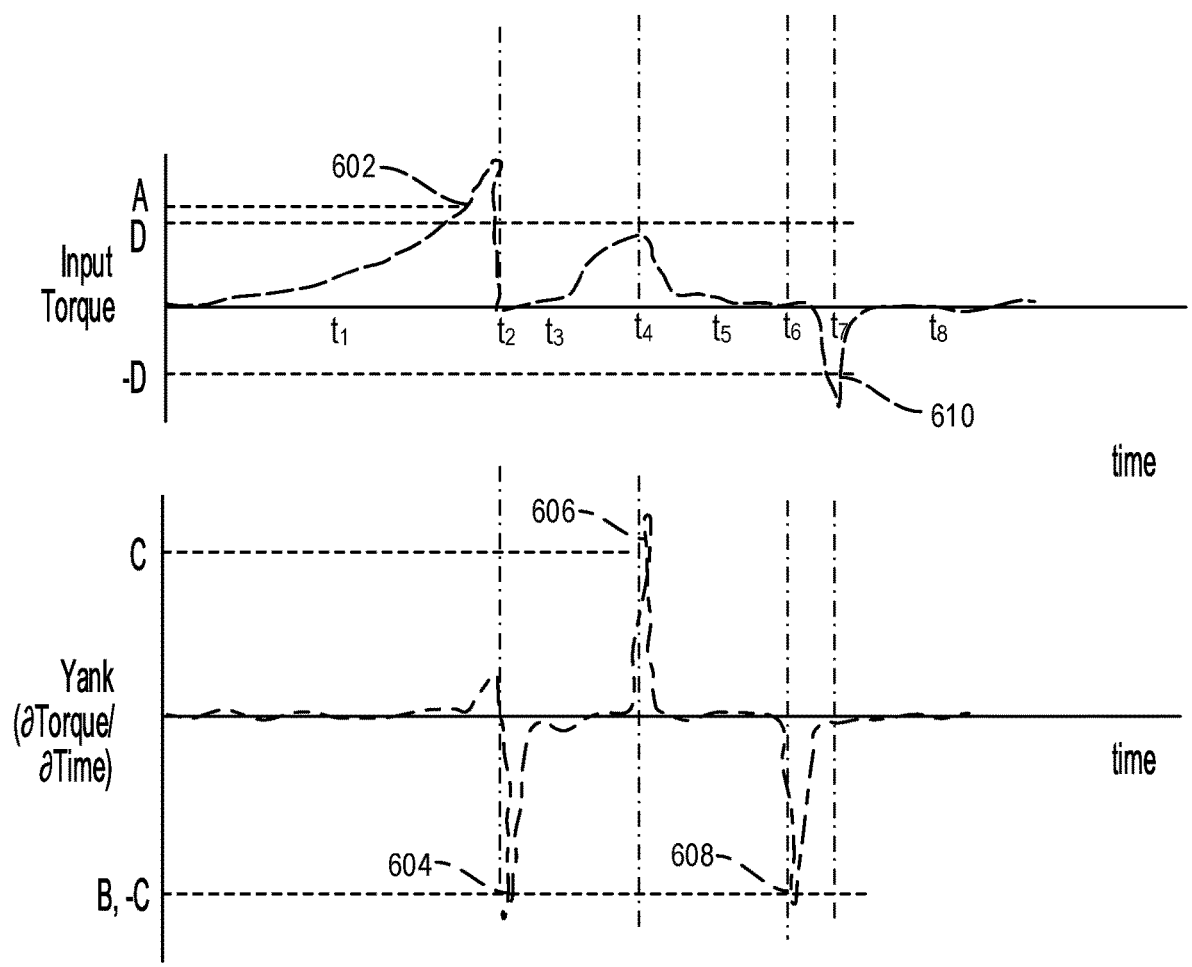

Referring now to FIGS. 19-21, a second example implementation of the impact mechanism 100 using algorithm 400 is provided, according to at least one aspect of the present disclosure. As can be in FIG. 20, for $t_1$, the rotary output 200 is driven by the rotary input 150, causing the angle of the rotary output 200 to change. As can be in FIG. 21, during $t_1$, the rotary output 200 begins to experience resistance, causing the input torque provided by the rotary input 150 to increase over $t_1$. At $t_2$, the input torque exceeds 602 torque threshold A, indicating that a potential slippage event has occurred. Accordingly, the control system detects the torque threshold A has been reached and proceeds 612 from block 404 to block 406 to verify if a slippage event actually occurred. As can be seen in FIG. 21, the control system determines that the yank of the impact mechanism 100 has dropped below 604 yank threshold −C, confirming that a slippage event in the first direction has actually occurred. Accordingly, the control system proceeds 614 from block 406 to block 408 to monitor for the rotary input 150 and the rotary output 200 returning to the coupled state.

As can be seen in FIG. 21, during $t_3$, since the rotary input 150 is rotating relative to the rotary output 200, no torque is being transferred to the rotary output 200. Leading up to $t_4$, the control system detects an increase in input torque from the rotary input 150 and a yank that exceeds 606 the yank threshold C, which is indicative of the impact mechanism 100 potentially returning to the coupled state. Accordingly, the control system proceeds 616 from block 408 to block 410 to determine if the impact mechanism actually returned to the coupled state.

At $t_4$, the control system detects an input torque from the rotary input 150 that is than torque threshold D. Accordingly, the control system does not proceed to block 412, rather, the control system continues to monitor the input torque of the rotary input 150 and the yank of the impact mechanism over time $t_5$. At time $t_6$, the control system detects a yank that is less than yank threshold −C, which is indicative of the rotary input 150 rotating in the opposite direction. In the example implementation of the impact mechanism 100, as can be seen in FIG. 21, the yank threshold B and yank threshold −C are identical. Accordingly, the control system proceeds 618 from block 410 to block 414 to decrement the slip count N and then proceeds to block 460 via block 458 to monitor for when the impact mechanism returns to the coupled state. At time $t_7$, the control system detects an input torque that drops below 610 torque threshold −D, indicating that the impact mechanism 100 has returned to the coupled state. Accordingly, the control mechanism proceeds 620 to block 462 and increment the slip count N. Overall, since the control system decremented the slip count at block 414 and incremented the slip count at 462, the control system can determine that the output angle of the rotary output has re-aligned with the input angle of the rotary input 150, as can be seen in FIG. 20.

While the above-described impact mechanism 100 and algorithm 400 were described in the context of a surgical stapling instrument with a rotary drive for driving multiple functions of an end effector, it should be understood that the impact mechanism 100 and the algorithm 400 can be applied in a variety of other applications, such as any suitable surgical instrument that transmits rotary motions from a motion generator (hand, motor, etc.) to a rotary output. The impact mechanism 100 can, thus, be utilized to provide brief peak loads to other rotary based systems. In various embodiments, for example, the impact mechanism can be used in an energy instrument, such as a radio-frequency instrument, to drive a knife within an end effector that includes electrodes for sealing tissue.

The surgical instrument systems described herein have been described in connection with the deployment and deformation of staples; however, the embodiments described herein are not so limited. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue.

The entire disclosures of:
U.S. patent application Ser. No. 16/553,725, entitled ARTICULATING INCLUDING ANTAGONISTIC CONTROLS FOR ARTICULATION AND CALIBRATION, filed Aug. 28, 2019, now U.S. Patent Application Publication No. 2021/0059777;
U.S. Pat. No. 5,403,312, entitled ELECTROSURGICAL HEMOSTATIC DEVICE, which issued on Apr. 4, 1995;
U.S. Pat. No. 7,000,818, entitled SURGICAL STAPLING INSTRUMENT HAVING SEPARATE DISTINCT CLOSING AND FIRING SYSTEMS, which issued on Feb. 21, 2006;

U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;

U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;

U.S. Pat. No. 7,670,334, entitled SURGICAL INSTRUMENT HAVING AN ARTICULATING END EFFECTOR, which issued on Mar. 2, 2010;

U.S. Pat. No. 7,753,245, entitled SURGICAL STAPLING INSTRUMENTS, which issued on Jul. 13, 2010;

U.S. Pat. No. 8,393,514, entitled SELECTIVELY ORIENTABLE IMPLANTABLE FASTENER CARTRIDGE, which issued on Mar. 12, 2013;

U.S. patent application Ser. No. 11/343,803, entitled SURGICAL INSTRUMENT HAVING RECORDING CAPABILITIES, now U.S. Pat. No. 7,845,537;

U.S. patent application Ser. No. 12/031,573, entitled SURGICAL CUTTING AND FASTENING INSTRUMENT HAVING RF ELECTRODES, filed Feb. 14, 2008;

U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;

U.S. patent application Ser. No. 12/235,782, entitled MOTOR-DRIVEN SURGICAL CUTTING INSTRUMENT, now U.S. Pat. No. 8,210,411;

U.S. patent application Ser. No. 12/235,972, entitled MOTORIZED SURGICAL INSTRUMENT, now U.S. Pat. No. 9,050,083.

U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;

U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009, now U.S. Pat. No. 8,220,688;

U.S. patent application Ser. No. 12/893,461, entitled STAPLE CARTRIDGE, filed Sep. 29, 2012, now U.S. Pat. No. 8,733,613;

U.S. patent application Ser. No. 13/036,647, entitled SURGICAL STAPLING INSTRUMENT, filed Feb. 28, 2011, now U.S. Pat. No. 8,561,870;

U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;

U.S. patent application Ser. No. 13/524,049, entitled ARTICULATABLE SURGICAL INSTRUMENT COMPRISING A FIRING DRIVE, filed on Jun. 15, 2012, now U.S. Pat. No. 9,101,358;

U.S. patent application Ser. No. 13/800,025, entitled STAPLE CARTRIDGE TISSUE THICKNESS SENSOR SYSTEM, filed on Mar. 13, 2013, now U.S. Pat. No. 9,345,481;

U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552;

U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

Various aspects of the subject matter described herein are set out in the following numbered examples:

Example 1—A surgical system comprising an end effector and a drive system configured to effect at least one function of the end effector. The end effector comprises a first jaw, a second jaw rotatable relative to said first jaw between an open configuration and a closed configuration, and a staple cartridge comprising staples removably stored therein. The drive system comprises a motor and an impact mechanism comprising a rotary input drivable by the motor and a rotary output drivable by the rotary input. Rotation of the rotary output is configured to effect the at least one function of the end effector. The impact mechanism is configurable between a coupled state, wherein rotation of the rotary input causes corresponding rotation of the rotary output and a slipped state, wherein the rotary input rotates relative to the rotary output.

Example 2—The surgical system of claim 1, wherein the rotary output comprises an output shaft and a head extending from the output shaft, wherein the head comprises a first ridge and a second ridge extending therefrom.

Example 3—The surgical system of claim 2, wherein the rotary input comprises an input shaft driveable by the motor and an impact driver comprising a base, a first arm extending from the base, wherein a first detent is defined in the first arm, and a second arm extending from the base, wherein a second detent is defined in the second arm.

Example 4—The surgical system of claim 3, wherein the first ridge is engaged with the first detent and the second ridge is engaged with the second detent, based on the impact mechanism being in the coupled state and the first ridge is disengaged from the first detent and the second ridge is disengaged from the second detent, based on the impact mechanism being in the slipped state.

Example 5—The surgical system of claim 3, wherein the rotary output is axially movable relative to the rotary input between an engaged position and a slipped position.

Example 6—The surgical system of claim 5, wherein the impact mechanism further comprises a spring configured to bias the rotary output toward the rotary input.

Example 7—The surgical system of claim 5, wherein the first arm and the second arm define a trough therebetween, and wherein the head is positionable in the trough based on the rotary output being in the slipped position.

Example 8—The surgical system of claim 5, wherein the first arm comprises a first cam surface, wherein the second arm comprises a second cam surface, and wherein the first cam surface and the second cam surface are configured to cooperatively cam the rotary output toward the engaged position based on rotation of the rotary input relative to the rotary output.

Example 9—The surgical system of claim 1, wherein the rotary input is configured to provide a first amount of torque to the rotary output based on the impact mechanism being in the coupled state, and wherein the rotary input is configured to provide a second amount of torque to the rotary output greater than the first amount of torque based on the impact mechanism being in the slipped state.

Example 10—A surgical system comprising an end effector and a drive system configured to effect at least one function of the end effector, wherein the drive system comprises an impact mechanism comprising a rotary input rotatable by a motion generator and a rotary output rotatable by the rotary input, wherein rotation of the rotary output is configured to effect the at least one function of the end effector. The impact mechanism is configurable between a coupled state, wherein the rotary input is configured to provide a first amount of torque to the rotary output and a slipped state, wherein the rotary input is configured to provide a second amount of torque to the rotary output greater than the first amount of torque.

Example 11—The surgical system of claim 10, wherein the rotary output comprises a head, wherein the rotary input comprises an impact driver, wherein the impact driver is coupled with the head in the coupled state, and wherein the impact driver is configured to rotate relative to and impact a lateral side of the head in the slipped state.

Example 12—A surgical system comprising an end effector and a drive system configured to effect at least one function of the end effector, wherein the drive system comprises an impact mechanism comprising a rotary output, wherein rotation of the rotary output is configured to effect the at least one function of the end effector and a rotary input configured to drive the rotary output. The impact mechanism is configurable between a coupled state, wherein rotation of the rotary input causes rotation of the rotary output and a slipped state, wherein the rotary input rotates relative to the rotary output. The impact mechanism is configurable to transition from the coupled state to the slipped state based on an occurrence of a slippage event. The impact mechanism is configured to transition from the slipped state to the coupled state based on the rotary input rotating a predetermined amount relative to the rotary output in the slipped state. The surgical system further comprises a control system configured to determine an amount of angular rotation transferred from the rotary input to the rotary output.

Example 13—The surgical system of claim 12, wherein the slippage event comprises a torque provided from the rotary input to the rotary output reaching or exceeding a torque threshold.

Example 14—The surgical system of claim 12, wherein the control system is configured to detect an occurrence of a slippage event, verify the occurrence of the slippage event, detect an occurrence of the impact mechanism reaching the coupled state, and verify the occurrence of the impact mechanism reaching the coupled state.

Example 15—The surgical system of claim 14, wherein detecting an occurrence of a slippage event comprises sensing a torque provided by the rotary input to the rotary output and comparing the sensed torque to a torque threshold. Verifying the occurrence of the slipped event comprises determining a yank associated with the impact mechanism and comparing the determined yank to a yank threshold.

Example 16—The surgical system of claim 15, wherein detecting an occurrence of the impact mechanism reaching the coupled state comprises determining a yank associated with the impact mechanism and comparing the determined yank to a yank threshold. Verifying the occurrence of the impact mechanism reaching the coupled state comprises sensing a torque provided by the rotary input to the rotary output and comparing the sensed torque to a torque threshold.

Example 17—The surgical system of claim 16, wherein the control system is further configured to set a slip count and adjust the slip count based on verifying the occurrence of the impact mechanism reaching the coupled state.

Example 18—The surgical system of claim 12, wherein the control system is further configured to set a slip count, set a correction angle associated with the impact mechanism, and determine an output angle of the rotary output relative to an input angle of the rotary input based on the correction angle and the slip count.

Example 19—The surgical system of claim 18, wherein the correction angle comprises an angle associated with the predetermined amount of rotation by the rotary input in the slipped state.

Example 20—The surgical system of claim 18, wherein the control system is configured to decrement the slip count based on the control system detecting a slippage event with the rotary input rotating a first direction and increment the slip count based on the control system detecting a slippage event with the rotary input rotating a second direction opposite the first direction.

Although various devices have been described herein in connection with certain embodiments, modifications and variations to those embodiments may be implemented. Particular features, structures, or characteristics may be combined in any suitable manner in one or more embodiments. Thus, the particular features, structures, or characteristics illustrated or described in connection with one embodiment may be combined in whole or in part, with the features, structures or characteristics of one ore more other embodiments without limitation. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, a device can be reconditioned for reuse after at least one use. Reconditioning can include any combination of the steps including, but not limited to, the disassembly of the device, followed by cleaning or replacement of particular pieces of the device, and subsequent reassembly of the device. In particular, a reconditioning facility and/or surgical team can disassemble a device and, after cleaning and/or replacing particular parts of the device, the device can be reassembled for subsequent use. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices disclosed herein may be processed before surgery. First, a new or used instrument may be obtained and, when necessary, cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, and/or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta radiation, gamma radiation, ethylene oxide, plasma peroxide, and/or steam.

While this invention has been described as having exemplary designs, the present invention may be further modified within the spirit and scope of the disclosure. This application is therefore intended to cover any variations, uses, or adaptations of the invention using its general principles.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" or "control system" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a system that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The term "substantially", "about", or "approximately" as used in the present disclosure, unless otherwise specified, means an acceptable error for a particular value as determined by one of ordinary skill in the art, which depends in part on how the value is measured or determined. In certain embodiments, the term "substantially", "about", or "approximately" means within 1, 2, 3, or 4 standard deviations. In certain embodiments, the term "substantially", "about", or "approximately" means within 50%, 20%, 15%, 10%, 9%, 8%, 7%, 6%, 5%, 4%, 3%, 2%, 1%, 0.5%, or 0.05% of a given value or range.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. A surgical system, comprising:
an end effector configured to receive a staple cartridge, wherein the end effector comprises:
a first jaw; and
a second jaw rotatable relative to said first jaw between an open configuration and a closed configuration;
a motor;
a rotary input drivable by the motor; and
a rotary output drivable by the rotary input, wherein rotation of the rotary output is configured to effect at least one function of the end effector;
wherein the rotary input and the rotary output are configurable between:
a coupled state in which rotation of the rotary input causes corresponding rotation of the rotary output; and
a slipped state in which the rotary input rotates relative to the rotary output;
wherein the rotary output is to experience a resistive torque in the coupled state, and wherein the rotary input and the rotary output are configured to transition from the coupled state to the slipped state based on the resistive torque exceeding a torque threshold.

2. The surgical system of claim 1, wherein the rotary output comprises:
an output shaft; and
a head extending from the output shaft, wherein the head comprises a first ridge and a second ridge extending therefrom.

3. The surgical system of claim 1, wherein the rotary input is configured to provide a first amount of torque to the rotary output based on the rotary input and the rotary output being in the coupled state, and wherein the rotary input is configured to provide a second amount of torque to the rotary output greater than the first amount of torque based on the rotary input and the rotary output being in the slipped state.

4. The surgical system of claim 1, further comprising a closure driver configured to rotate the second jaw toward the closed configuration based on rotation of the rotary output.

5. The surgical system of claim 1, further comprising a firing driver configured to deploy staples from the staple cartridge based on rotation of the rotary output.

6. The surgical system of claim 1, further comprising a knife configured to translate through the end effector based on rotation of the rotary output.

7. The surgical system of claim 1, further comprising a shifter, shiftable between:
a first state in which rotation of the rotary output is configured to effect a first end effector function; and
a second state in which rotation of the rotary output is configured to effect a second end effector function different than the first end effector function.

8. A surgical system, comprising:
an end effector configured to receive a staple cartridge, wherein the end effector comprises:
a first jaw; and
a second jaw rotatable relative to said first jaw between an open configuration and a closed configuration;
a motor;
a rotary input drivable by the motor; and
a rotary output drivable by the rotary input, wherein rotation of the rotary output is configured to effect at least one function of the end effector;
wherein the rotary input and the rotary output are configurable between:
a coupled state in which rotation of the rotary input causes corresponding rotation of the rotary output; and
a slipped state in which the rotary input rotates relative to the rotary output;
wherein the rotary output comprises:
an output shaft; and
a head extending from the output shaft, wherein the head comprises a first ridge and a second ridge extending therefrom; and
wherein the rotary input comprises:
an input shaft driveable by the motor; and
an impact driver, comprising:
a base;
a first arm extending from the base, wherein a first detent is defined in the first arm; and
a second arm extending from the base, wherein a second detent is defined in the second arm.

9. The surgical system of claim 8, wherein:
the first ridge is engaged with the first detent and the second ridge is engaged with the second detent based on the rotary input and the rotary output being in the coupled state; and
the first ridge is disengaged from the first detent and the second ridge is disengaged from the second detent based on the rotary input and the rotary output being in the slipped state.

10. The surgical system of claim 8, wherein the rotary output is axially movable relative to the rotary input between an engaged position and a slipped position.

11. The surgical system of claim 10, further comprising a spring configured to bias the rotary output toward the rotary input.

12. The surgical system of claim 10, wherein the first arm and the second arm define a trough therebetween, and wherein the head is positionable in the trough based on the rotary output being in the slipped position.

13. The surgical system of claim 10, wherein the first arm comprises a first cam surface, wherein the second arm comprises a second cam surface, and wherein the first cam surface and the second cam surface are configured to cooperatively cam the rotary output toward the engaged position based on rotation of the rotary input relative to the rotary output.

14. A surgical system, comprising:
an end effector, comprising:
a first jaw; and
a second jaw rotatable relative to the first jaw to capture tissue therebetween; and
a rotary input rotatable by a motion generator; and
a rotary output rotatable by the rotary input, wherein rotation of the rotary output is configured to effect at least one function of the end effector; and
wherein the rotary input and the rotary output are configurable between:
a coupled state in which the rotary input is configured to provide a first torque to the rotary output; and
a slipped state in which the rotary input is configured to provide a second of torque to the rotary output greater than the first torque;
wherein the rotary output is to experience a resistive torque in the coupled state, and wherein the rotary input and the rotary output are configured to transition from the coupled state to the slipped state based on the resistive torque exceeding a torque threshold.

15. The surgical system of claim 14, wherein the rotary output comprises a head, wherein the rotary input comprises an impact driver, wherein the impact driver is coupled with the head in the coupled state, and wherein the impact driver is configured to rotate relative to and impact a lateral side of the head in the slipped state.

16. A surgical system, comprising:
   an end effector, comprising:
      a first jaw; and
      a second jaw rotatable relative to the first jaw;
   a rotary output, wherein rotation of the rotary output is configured to effect at least one function of the end effector;
   a rotary input configured to drive the rotary output;
   wherein the rotary input and the rotary output are configurable between:
      a coupled state in which rotation of the rotary input causes rotation of the rotary output; and
      a slipped state in which the rotary input rotates relative to the rotary output, wherein the rotary input and the rotary output are configured to transition from the coupled state to the slipped state based on an occurrence of a slippage event, wherein the rotary input and the rotary output are configured to transition from the slipped state to the coupled state based on the rotary input rotating a predetermined amount relative to the rotary output in the slipped state; and
   a control circuit to determine an amount of angular rotation transferred from the rotary input to the rotary output.

17. The surgical system of claim 16, wherein the slippage event comprises a torque provided from the rotary input to the rotary output reaching or exceeding a torque threshold.

18. The surgical system of claim 16, wherein the control circuit is to:
   detect an occurrence of a slippage event;
   verify the occurrence of the slippage event;
   detect an occurrence of the rotary input and the rotary output reaching the coupled state; and
   verify the occurrence of the rotary input and the rotary output reaching the coupled state.

19. The surgical system of claim 18, wherein:
   detecting an occurrence of a slippage event comprises:
      sensing a torque provided by the rotary input to the rotary output; and
      comparing the sensed torque to a torque threshold; and
   verifying the occurrence of the slipped event comprises:
      determining a yank associated with the rotary input and the rotary output; and
      comparing the determined yank to a yank threshold.

20. The surgical system of claim 19, wherein:
   detecting an occurrence of the rotary input and the rotary output reaching the coupled state comprises:
      determining a yank associated with the rotary input and the rotary output; and
      comparing the determined yank to a yank threshold; and
   verifying the occurrence of the rotary input and the rotary output reaching the coupled state comprises:
      sensing a torque provided by the rotary input to the rotary output; and
      comparing the sensed torque to a torque threshold.

21. The surgical system of claim 16, further comprising a closure driver configured to rotate the second jaw relative to the first jaw based on rotation of the rotary output.

22. The surgical system of claim 16, further comprising a knife configured to translate through the end effector based on rotation of the rotary output.

23. The surgical system of claim 16, further comprising a shifter, shiftable between:
   a first state in which rotation of the rotary output is configured to effect a first end effector function; and
   a second state in which rotation of the rotary output is configured to effect a second end effector function different than the first end effector function.

24. A surgical system, comprising:
   an end effector;
   a rotary output, wherein rotation of the rotary output is configured to effect at least one function of the end effector;
   a rotary input configured to drive the rotary output;
   wherein the rotary input and the rotary output are configurable between:
      a coupled state in which rotation of the rotary input causes rotation of the rotary output; and
      a slipped state in which the rotary input rotates relative to the rotary output, wherein the rotary input and the rotary output are configured to transition from the coupled state to the slipped state based on an occurrence of a slippage event, wherein the rotary input and the rotary output are configured to transition from the slipped state to the coupled state based on the rotary input rotating a predetermined amount relative to the rotary output in the slipped state; and
   a control circuit to determine an amount of angular rotation transferred from the rotary input to the rotary output;
   wherein the control circuit is further to:
      detect an occurrence of a slippage event;
      verify the occurrence of the slippage event;
      detect an occurrence of the rotary input and the rotary output reaching the coupled state; and
      verify the occurrence of the rotary input and the rotary output reaching the coupled state;
   wherein:
      detecting an occurrence of a slippage event comprises:
         sensing a torque provided by the rotary input to the rotary output; and
         comparing the sensed torque to a torque threshold; and
      verifying the occurrence of the slipped event comprises:
         determining a yank associated with the rotary input and the rotary output; and
         comparing the determined yank to a yank threshold
   wherein:
      detecting an occurrence of the rotary input and the rotary output reaching the coupled state comprises:
         determining a yank associated with the rotary input and the rotary output; and
         comparing the determined yank to a yank threshold; and
      verifying the occurrence of the rotary input and the rotary output reaching the coupled state comprises:
         sensing a torque provided by the rotary input to the rotary output; and
         comparing the sensed torque to a torque threshold; and
   wherein the control circuit is further to:
      set a slip count; and
      adjust the slip count based on verifying the occurrence of the rotary input and the rotary output reaching the coupled state.

25. A surgical system, comprising:
an end effector;
a rotary output, wherein rotation of the rotary output is configured to effect at least one function of the end effector;
a rotary input configured to drive the rotary output;
wherein the rotary input and the rotary output are configurable between:
　a coupled state in which rotation of the rotary input causes rotation of the rotary output; and
　a slipped state in which the rotary input rotates relative to the rotary output, wherein the rotary input and the rotary output are configured to transition from the coupled state to the slipped state based on an occurrence of a slippage event, wherein the rotary input and the rotary output are configured to transition from the slipped state to the coupled state based on the rotary input rotating a predetermined amount relative to the rotary output in the slipped state; and
a control circuit to determine an amount of angular rotation transferred from the rotary input to the rotary output;
　wherein the control circuit is further to:
　　set a slip count;
　　set a correction angle associated with the rotary input and the rotary output; and
　　determine an output angle of the rotary output relative to an input angle of the rotary input based on the correction angle and the slip count.

26. The surgical system of claim 25, wherein the correction angle comprises an angle associated with the predetermined amount of rotation by the rotary input in the slipped state.

27. The surgical system of claim 25, wherein the control circuit is further to:
　decrement the slip count based on the control circuit detecting a slippage event with the rotary input rotating a first direction; and
　increment the slip count based on the control circuit detecting a slippage event with the rotary input rotating a second direction opposite the first direction.

\* \* \* \* \*